United States Patent [19]

Urry et al.

[11] Patent Number: 4,783,523

[45] Date of Patent: Nov. 8, 1988

[54] TEMPERATURE CORRELATED FORCE AND STRUCTURE DEVELOPMENT OF ELASTIN POLYTETRAPEPTIDES AND POLYPENTAPEPTIDES

[76] Inventors: Dan W. Urry, 2423 Vestavia Dr., Birmingham, Ala. 35216; K. U. M. Prasad, 310 Cedar Path Dr., Birmingham, Ala. 35209

[21] Appl. No.: 900,895

[22] Filed: Aug. 27, 1986

[51] Int. Cl.$^4$ .................... C07K 5/02; D02G 3/00
[52] U.S. Cl. .................... 530/323; 530/324; 530/328; 530/330; 530/350; 428/373
[58] Field of Search ............... 530/330, 323, 324, 350; 528/328; 428/373

[56] References Cited

U.S. PATENT DOCUMENTS

| | | | |
|---|---|---|---|
| 4,132,746 | 1/1979 | Urry | 528/328 |
| 4,474,851 | 10/1984 | Urry | 428/373 |
| 4,500,700 | 2/1985 | Urry | 528/328 |
| 4,589,882 | 5/1986 | Urry | 530/330 |

OTHER PUBLICATIONS

Chem. Abstr., vol. 106, (1987), 171320.
Chem. Abstr., vol. 105, (1986), 93078.
Chem. Abstr., vol. 102, (1985), 185485.
Chem. Abstr., vol. 103, (1985), 83723.
Chem. Abstr., vol. 100, (1984), 197695.
Chem. Abstr., vol. 99, (1983), 6026.
Chem. Abstr., vol. 96, (1982), 187225.
Chem. Abstr., vol. 91, (1979), 205876.

*Primary Examiner*—Delbert R. Phillips
*Attorney, Agent, or Firm*—Oblon, Fisher, Spivak, McClelland & Maier

[57] ABSTRACT

A bioelastomer containing elastomeric units comprising tetrapeptide, or pentapeptide or units thereof modified by hexapeptide repeating units and mixtures thereof, wherein said repeating units comprise amino acid residues selected from the group consisting of hydrophobic amino acid and glycine residues, wherein said repeating units exist in a conformation having a $\beta$-turn which comprises a polypentapeptide unit of the formula:

$$-X^1-(IPGVG)_n-Y^1-$$

wherein
I is a peptide-forming residue of L-isoleucine;
P is a peptide-forming residue of L-proline;
G is a peptide-forming residue of glycine;
V is a peptide-forming residue of L-valine; and wherein $X^1$ is PGVG, GVG, VG, G or a covalent bond; $Y^1$ is IPGV, IPG, IP, I or a covalent bond; and n is an integer from 1 to 200, or n is 0, with the proviso that $X^1$ and $Y^1$ together constitute at least one of said pentameric unit, in an amount sufficient to adjust the development of elastomeric force of the bioelastomer to a predetermined temperature.

24 Claims, 10 Drawing Sheets

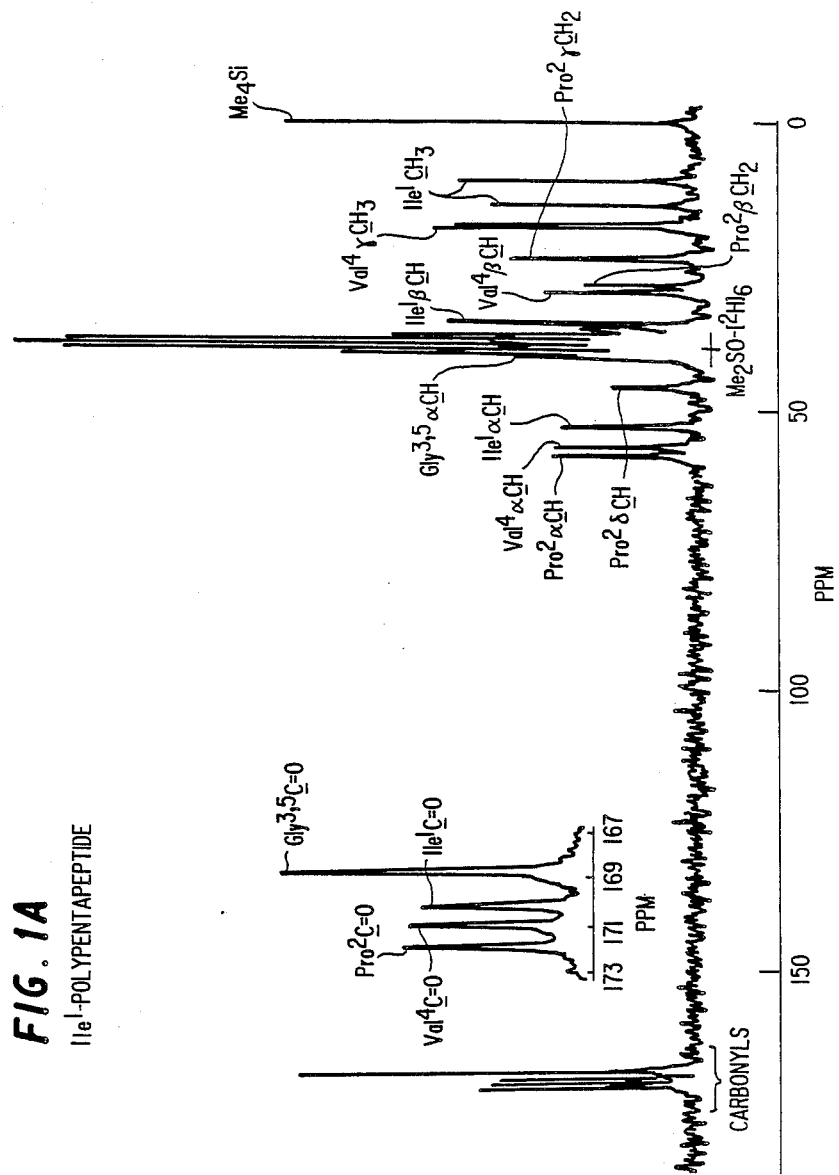

POLYPENTAPEPTIDE

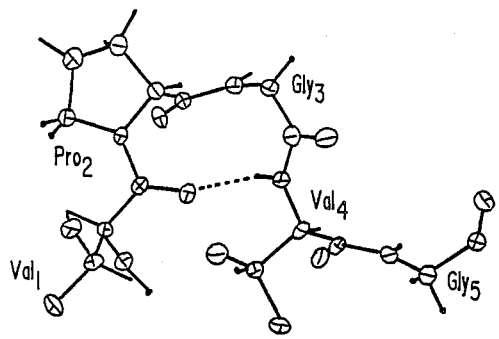
β - TURN PERSPECTIVE
FIG. 4A
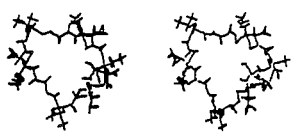
β - SPIRAL OF THE
POLYPENTAPEPTIDE
OF ELASTOLIN
FIG. 4D AXIS VIEW
FIG. 4B     FIG. 4C
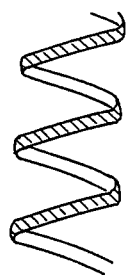 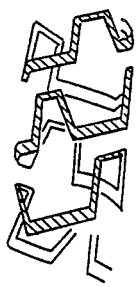
SCHEMATIC
REPRESENTATIONS
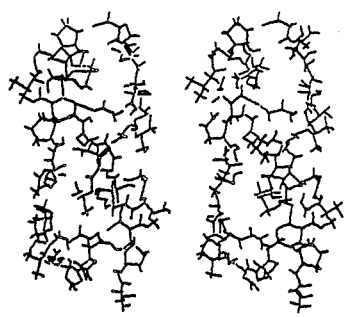
FIG. 4E SIDE VIEW

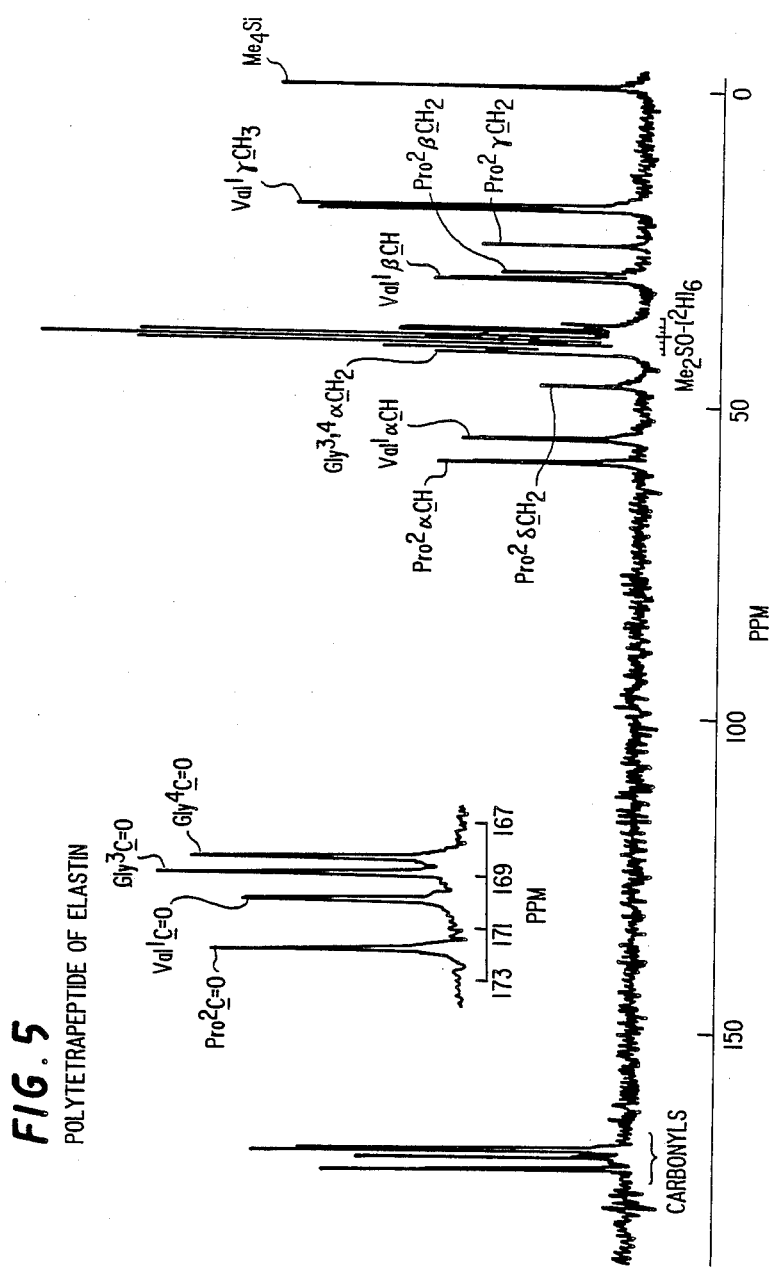

TEMPERATURE CORRELATED FORCE AND STRUCTURE DEVELOPMENT OF ELASTIN POLYTETRAPEPTIDES AND POLYPENTAPEPTIDES

BACKGROUND OF THE INVENTION

The government has rights in this invention as a result of the work described herein being supported in part by the National Institutes of Health under Grant No. HL-29578.

FIELD OF THE INVENTION

This invention relates to bioelastomers, particularly to bioelastomers which can be used as replacements for elastin, and more particularly to bioelastomers which exhibit controllable elastomeric force development as a function of temperature.

DESCRIPTION OF THE BACKGROUND

The connective tissue of vascular walls is formed from two principal types of protein. Collagen, in general, the principal proteinaceous component of connective tissue, constitutes the structural element imparting strength to the tissue. However, where the demand for elasticity is great as in the aortic arch and descending thoracic aorta, there is twice as much elastin as collagen. In the vascular wall, and particularly in the internal elastic lamina thereof, collagen is associated with natural elastic fibers formed from a different type of protein, known as tropoelastin. In the relaxed vascular wall, collagen fibers tend to be folded or crimped, and the elastic fibers are in a retracted state. Upon distention or stretching, the elastic fibers become stretched, and, before their extension limit is approached, the collagen fibers come into tension to bear the load. As the load diminishes, the elastic fibers draw the wall back to its original dimension and the collagen fibers back into a folded state.

The above can also be demonstrated experimentally, for if the collagen component of an intact ligament is removed in vitro by the enzyme collagenase, the resultant stress-strain relationship clearly indicates that the elastic component, elastin, is principally responsible for the initial high yield response of the intact ligament. Conversely, removal of elastin by the enzyme elastase leaves collagen which is observed to be responsible for only the final portion of the response of the intact ligament. See *Introductory Biophysics*, F. R. Hallett et al. (Halsted Press, 1977).

Presently available synthetic vascular materials, such as Dacron, are quite different from natural connective tissue in that the synthetic weave can be viewed as providing the structural analog of folded collagen, but there is no true elastomeric component therein.

The central portion of the elastic fibers of vascular wall, skin, lung and ligament is derived from a single protein called tropoelastin. Elastin, the actual elastomeric component of biological elastic fibers, is composed of a single protein and is formed from the cross-linking of the lysine residues of tropoelastin. The sequence of elastin can be described as a serial alignment of alanine-rich, lysine-containing cross-linking sequences alternating with glycine-rich hydrophobic sequences. More than 80% of the elastin sequence is known, and it has been shown that vascular wall tropoelastin contains a repeat hexapeptide (Ala-Pro-Gly-Val-Gly-Val)$_n$, a repeat pentapeptide (Val-Pro-Gly-Val-Gly)$_n$, and a repeat tetrapeptide (Val-Pro-Gly-Gly)$_n$ where Ala, Pro, Val and Gly, respectively, represent alanine, proline, valine, and glycine amino acid residues. These residues can also be represented, respectively, as A, P, V and G, inasmuch as amino acids can be referred to either by standard three-letter or one-letter abbreviations. See, for example, *Organic Chemistry of Biological Compounds*, pages 56–58 (Prentice-Hall, 1971). Further, in this application, all peptide representations conform to the standard practice of writing the NH$_2$-terminal amino acid residue on the left of the formula and the CO$_2$H-terminal amino acid residue on the right. Furthermore, unless otherwise specified all amino acids are of the L-configuration, with the exception of Glycine, which is optically inactive.

The nature of the amino acid sequence in the vicinity of the tropoelastin cross-links is also known. Moreover, a high polymer of the hexapeptide has been synthesized, and found to form cellophane-like sheets. In view of this, and its irreversible association on raising the temperature in water, the hexapeptide is, therefore, thought to provide a structural role in the natural material. On the other hand, synthetic high polymers of the pentapeptide and of the tetrapeptide have been found to be elastomeric when cross-linked and have the potential to contribute to the functional role of the elastic fiber. In fact, the chemically cross-linked polypentapeptide can, depending upon its water content and degree of cross-linking, exhibit the same elastic modulus as native aortic elastin.

More recently, a synthetic polypentapepide based on the pentapeptide sequence disclosed above was disclosed and claimed in U.S. Pat. No. 4,187,852 to Urry and Okamoto. Furthermore, a composite bioelastic material based on an elastic polypentapeptide or polytetrapeptide and a strength-giving fiber was disclosed and claimed in U.S. Pat. No. 4,474,851 to Urry. Additionally, a bioelastic material having an increased modulus of elasticity formed by replacing the third amino acid in a polypentapeptide with an amino acid of opposite chirality was disclosed and claimed in U.S. Pat. No. 4,500,700 to Urry and to an enzymatically cross-linked polypeptide as disclosed in and claimed in U.S. Pat. No. 4,589,882. Finally, it is also noted that at present, Ser. No. 533,670, directed to a chemotactic peptide and Ser. No. 793,225, directed to a second chemotactic peptide are both pending. Also pending is Ser. No. 853,212, directed to a segmented polypeptide bioelastomer for the modulation of elastic modulus.

At present, there is a tremendous demand for new synthetic vascular materials and prostheses. Hence, there is a consequent demand for new bioelastic materials based on the above-described polypentapeptide and polytetrapeptide repeating sequences which have desirable, but modified chemical and biological characteristics. This demand is, perhaps, due to the ubiquitous nature of elastin in the human body and the implications thereof. For example, in the extracellular matrix of the vascular wall, the elastin fiber is a primary site of lipid deposition contributing to the gruel of atherosclerosis. Further, in pulmonary emphysema, elastin fibers are disrupted and rendered dysfunctional. Additionally, it can be noted that there are many disease states involving elastin fibers and dysfunctions thereof, for example, the heritable disorders such as pseudoxanthoma elasticum, cutis laxa, endocardial fibroelastosis, and the Buscke-Ollendorf, Ehlers-Danlos, Menkes, and Marfans syndromes. Furthermore, elastin fiber dysfunction is also implicated in the acquired diseases: actinic elastosis, isolated elastomas, elastofibroma dorsi and elastosis perforans serpiginosa. Even from a purely cosmetic standpoint, it is known that solar elastosis of the dermis contributes to the wrinkles of age, and underlying the wrinkles, the elastin fibers are found to be ruptured. Clearly, the development of new synthetic polypentapeptide and polytetrapeptide elastomers would provide, for the first time, versatile substitutes for damaged natural elastin fibers as well as new methods for treating these various diseases.

However, until recently, little has been known about the elastic properties of the bioelastomeric polytetrapeptides and polypentapeptides. Thus, the rational design of specific bioelastomers for particular structural purposes has been extremely limited. For example, up until the present, it has not been possible to vary the temperature range over which would occur the elastomeric force development of synthetic bioelastomers. It would seem that such control would be imperative in order to rationally design a suitable bioelastomeric material for a given purpose. For example, in order to design a thermomechanical transducer for a predetermined temperature, it is necessary to provide materials which development elastomeric force within different temperature ranges.

It is difficult to underestimate the importance of selecting the right material for a particular biological or industrial function. For example, in *Technology Review,* Nov./Dec. 1984 (Edited at MIT), it was noted that a major obstacle to the development of a reliable artificial heart, as well as prosthetic devices generally, was the lack of suitable synthetic biomaterials. In the case of the artificial heart, it was found that calcium was deposited therein to an unacceptable extent, among other problems. Quite appropriately, Bronowski has noted in his Olympian work the *Ascent of Man,* that:

In effect the modern problem is no longer to design a structure from the materials but to design materials for a structure.

However, before bioelastic materials can be rationally designed for particular biological purposes requiring variable elasticity, it will be necessary to provide a means for rationally controlling the elastomeric force development of the bioelastomer. Thus, it would be extremely desirable to provide a means for controlling the elastomeric force development of the bioelastomers as a function of temperature. This would greatly broaden the variety of environments in which such materials could function. At present, no such control is possible.

Accordingly, in general, a need clearly continues to exist for bioelastic materials based on polypentapeptide and polytetrapeptide repeating sequences which exhibit desirable chemical and biological characteristics. In particular, a need continues to exist for such bioelastic materials, the elastomeric force development of which can be controlled and varied as a function of temperature.

SUMMARY OF THE INVENTION

Accordingly, it is an object of the present invention to provide elastomeric polymers which exhibit an elastomeric force development which can be varied as a function of temperature.

Additionally, it is also an object of this invention to provide a method of making elastomeric polymers which exhibit elastomeric force development which can be varied as a function of temperature.

These and other objects of the invention as will hereinafter become more readily apparent have been accomplished, in part, by providing a bioelastomer containing elastomeric units comprising tetrapeptide, pentapeptide and units thereof modified by hexapeptide repeating units and mixtures thereof, wherein said repeating units comprise amino acid residues selected from the group consisting of hydrophobic amino acid and glycine residues, wherein said repeating units exist in a conformation having a $\beta$-turn which comprises a polypentapeptide unit of the formula:

wherein

I is a peptide-forming residue of L-isoleucine;
P is a peptide-forming residue of L-proline;
G is a peptide-forming residue of glycine;
V is a peptide-forming residue of L-valine; and wherein $X^1$ is PGVG, GVG, VG, G or a covalent bond;

$Y^1$ is IPGV, IPG, IP, I or a covalent bond; and n is an integer from 1 to 200, or n is 0, with the proviso that $X^1$ and $Y^1$ together constitute a repeating pentapeptide unit, in an amount sufficient to adjust the development of elastomeric force of the bioelastomer to a predetermined temperature.

Figure 1B:
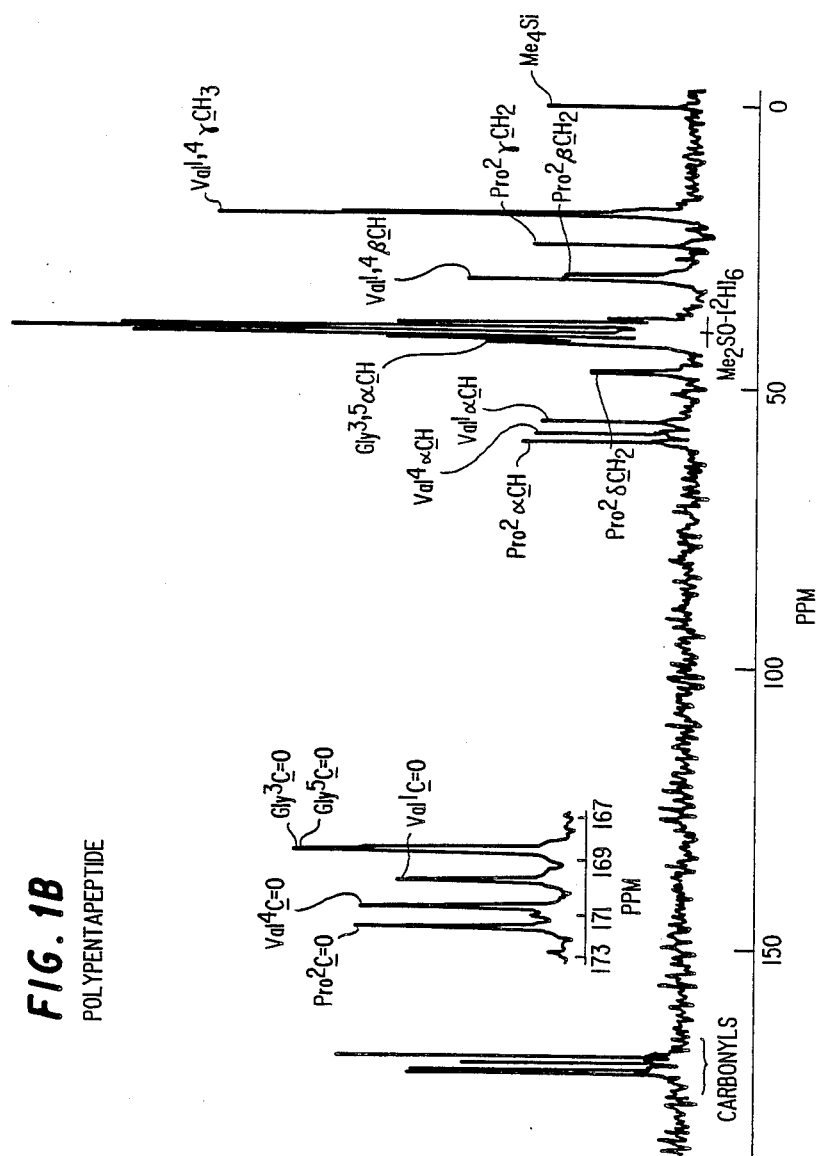
FIG. 1

Carbon-13 NMR spectra at 25 MHz in dimethylsulfoxide for A. $Ile^1$-PPP and B. PPP. These spectra demonstrate the replacement of $Val^1$ by $Ile^1$; particularly in the upfield region the replacements of the $\beta$ and $\gamma$ carbon resonances of one valine residue by the $CH_2$ and $CH_3$ resonances of isoleucine are apparent. The lack of extraneous peaks indicates a good level of purity and the similar chemical shifts of the other four residues indicate similar conformations in this solvent.

FIG. 2

A. Temperature profiles for coacervation for the $Ile^1$-PPP showing the high concentration limit to have an onset of aggregation at about 8° C. and a midpoint at 9° C. On dilution the profiles shift to higher temperatures. The polypentapeptide of elastin (PPP) profiles are given for comparison as the dashed curves. The addition of a $CH_2$ moiety causes a shift by 16° C. to lower temperatures for the coacervation process.

B. Ellipticity data at 197 nm for 0.025 mg $Ile^1$-PPP per ml given as the solid curve. The decrease in magnitude of the negative 197 nm band indicates an increase in intramolecular order on increasing the temperature, i.e., an inverse temperature transition. The dashed curve is the same data for 2.3 mg PPP per ml. The replacement of $Val^1$ by $Ile^1$ shifts the transition 15° C. or more to lower temperatures.

C. Thermoelasticity data (temperature dependence of elastomeric force) for 20 Mrad $\gamma$-irradiation cross-linked $Ile^1$-PPP coacervate shown as the solid curve. There is a dramatic increase in elastomeric force that correlates with the transition characterized in A and B above. Similar data for 20 Mrad cross-linked PPP coacervate are plotted on the right-hand ordinate as the dashed curve. The difference in scales is due to the smaller cross-sectional area and a 40% extension for cross-linked Ile[1]-PPP whereas a larger cross-sectional area and a 60% extension were used for cross-linked PPP. The elastic moduli are similar for the two elastomers. Comparing the data in parts A, B, and C, it is apparent that the increased hydrophobicity of Ile over Val causes the inverse temperature transition to occur at lower temperatures and that the elastomeric force development occurs as a result of increased intramolecular order.

FIG. 3

Circular dichroism spectra for 0.025 mg Ile[1]-PPP per ml of water at 2° C. (curve a) before the transition seen in FIG. 2B and at 35° C. (curve b) after the transition. As the large negative band near 195 nm is indicative of decreased polypentapeptide order, the decreased magnitude of the large negative band on increasing the temperature is indicative of increased order on raising the temperature. The spectrum at elevated temperature is indicative of Type II $\beta$-turn formation. For comparison is data for PPP at 0.023 mg/ml at 15° C. before and 47° C. after the transition shown in FIG. 2C. It is clear that Ile[1]-PPP and PPP have the same conformation.

FIG. 4

Molecular structure proposed for the polypentapeptide of elastin (PPP).

A. The Type II Pro[2]-Gly[3] $\beta$-turn as confirmed by the crystal structure of the cyclic conformational correlate.

B. Schematic representation of a helix with dimensions of the PPP $\beta$-spiral.

C. Schematic representation of the PPP $\beta$-spiral showing the $\beta$-turns to function as spacers between turns of the spiral.

D. Detailed stereo pair of the axis view of the PPP $\beta$-spiral showing space within the spiral for water and showing the Val[4]-Gly[5]-Val[1] suspended segment.

E. Stereo pair side view of the $\beta$-spiral of the PPP showing the $\beta$-turns functioning as spacers between turns of the spiral, showing open spaces on the surface of the $\beta$-spiral wherein intraspiral and extraspiral water can exchange, and showing the suspended segment, Val[4]-Gly[5]-Val[1].

FIG. 5

Carbon-13 nuclear magnetic resonance spectrum at 25 MHz in dimethylsulfoxide of the polytetrapeptide of elastin prepared by polymerization of the GGVP permutation. All the carbon resonances are observed with the correct chemical shifts and there are no extraneous peaks.

FIG. 6

Temperature profiles for coacervation of the polytetrapeptide (PTP) of elastin for a series of concentrations (the solid curves). For comparison are data for the polypentapeptide (PPP) of elastin (dashed curves). The decreased hydrophobicity of the tetramer (VPGG) when compared to the pentamer (VPGVG) results in a shift to higher temperature by some 25° C. for the aggregational process leading to coacervate formation.

FIG. 7

Circular dichroism spectra for the PTP of elastin (solid curves) at low temperature 40° C. (curve a) and at elevated temperature 65° (curve b). The structural transition giving rise to the difference in the 195-200 nm range is characterized as a function of temperature in FIG. 4A. Plotted for comparison is data for the PPP (dashed curves) before and after the transition shown in FIG. 4A.

FIG. 8

A. Ellipticity at 200 nm as a function of temperature of the PTP of elastin (solid curve) plotted on left-hand ordinate. For comparison are the data for PPP (dashed curve) plotted on the right-hand ordinate. The structural transition is seen to occur for the PTP at a higher temperature by 20° to 25° C. The center of the transition corresponds with the aggregational process in FIG. 2, that is, the intramolecular conformational change precedes the association giving rise to coacervation. As seen on comparison with part B, the characterization of the intramolecular structural transition by $[\theta]_{200}$ closely parallels the development of elastomeric force.

B. Thermoelasticity data (temperature dependence of elastomeric force) for the 20 Mrad cross-linked PTP (solid curve) plotted on left-hand ordinate and for comparison for the 20 Mrad cross-linked PPP (dashed curve) plotted on right-hand ordinate. The transition in elastomeric force is seen to correspond to the inverse temperature transition in intramolecular order as characterized by ellipticity in A above.

FIG. 9

Figure 2:
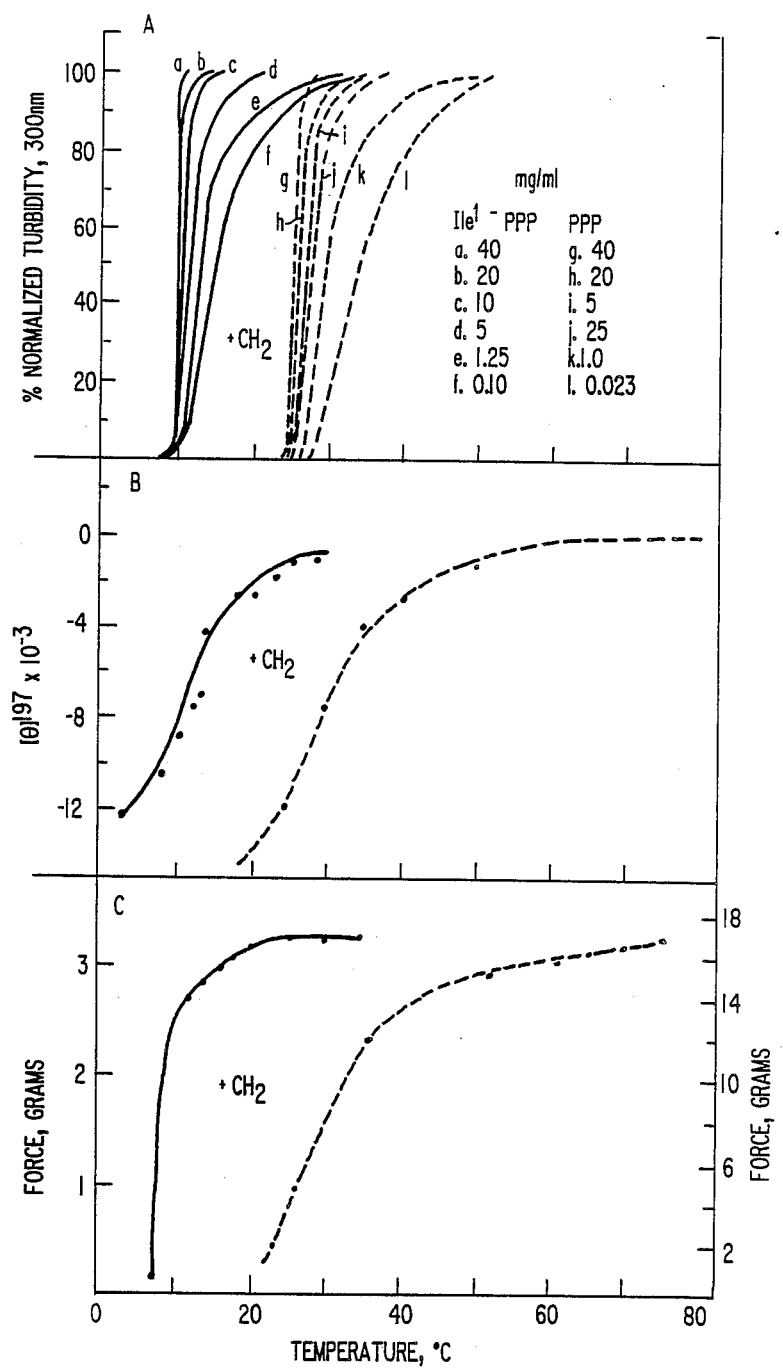
Figure 8:
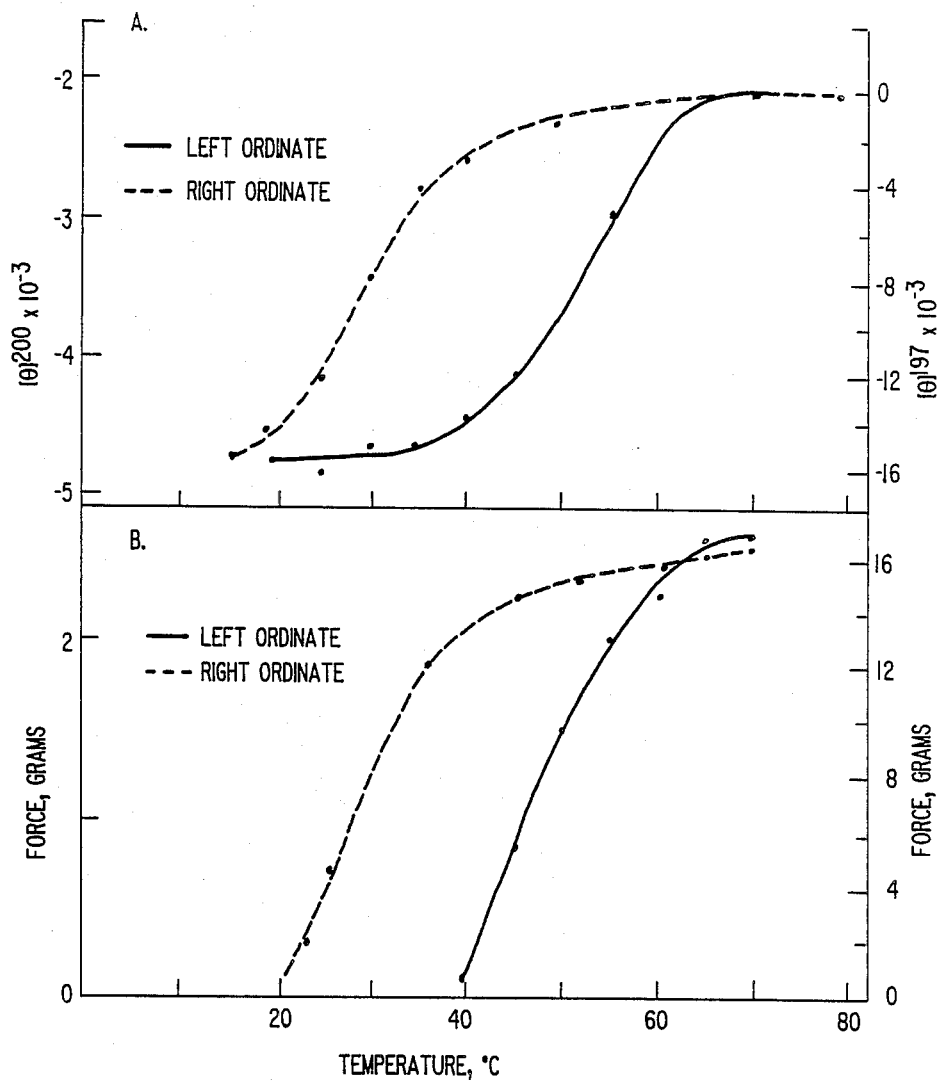

Scale representations of the hydrophobicities of the repeating units (IPGVG), (VPGVG) and (VGPP) shown along with the midpoint temperatures of the transitions as approximated from the ellipticity data ($[\theta]$ transition midpoint) and by the elastomeric force data (f transition midpoint) of FIGS. 2 and 8. This demonstrates that as the hydrophobicity of the repeating unit decreases the temperature for the transition shifts proportionately to higher temperatures. As an inverse temperature transition in water is due to hydrophobic interactions, this verifies that the transition temperature correlates very closely with hydrophobicity of the repeating unit.

DESCRIPTION OF THE PREFERRED EMBODIMENTS

As noted above, elastin is comprised of a single protein. The sequence of elastin can be described as a serial alignment of alanine-rich, lysine-containing cross-linking sequences alternating with glycine-rich hydrophobic sequences. With more than 80% of the sequence known, the most striking hydrophobic sequences, both from the standpoint of length and of composition, are one that contains a polypentapeptide (PPP) and one that contains a polyhexapeptide (PHP). Elastin also contains a repeating polytetrapeptide (PTP). As a result of work conducted by the present inventors, the polypentapeptide of elastin when cross-linked has been found to be elastomeric and the polyhexapeptide thereof has been found to be non-elastomeric and appears to provide a means for aligning and interlocking the chains during elastogenesis. From the present work, it has now also been found that the elastin polypentapeptide and polytetrapeptide are both conformation-based elastomers that develop entropic elasticity on undergoing an inverse temperature transition to form a regular $\beta$-turn containing dynamic structure.

A typical biological elastic fiber is comprised of a large elastin core covered with a fine surface layer of microfibrillar protein. As noted previously, elastin is formed upon cross-linking of the lysine residues of tropoelastin. The repeating elastin pentapeptide has the formula $(VPGVG)_n$, while the repeating hexapeptide has the formula $(VAPGVG)_n$, where n varies depending upon the species. The repeating polytetrapeptide unit has the formula $(VPGG)_n$. These sequences, of course, utilize the standard one-letter abbreviation for the constituent amino acids.

It has been found that these polypeptides are soluble in water below 25° C., but on raising the temperature they associate in the polypentapeptide (PPP) and polytetrapeptide (PTP) cases, reversibly to form a viscoelastic phase, and in the polyhexapeptide (PHP) case, irreversibly to form a precipitate. On cross-linking, the former (PPP) and (PTP) have been found to be elastomers.

In part, the present invention resides in the dsscovery that at temperatures above 25° C. in water, PTP and PPP exhibit aggregation and form a water-containing viscoelastic phase, which upon cross-linking by γ-irradiation forms an elastomer. By contrast, PHP forms a granular precipitate, which is not elastomeric. In fact, it has been found that for potential elastomers, such aggregation is readily reversible, whereas for non-elastomeric samples, such as PHP, temperature-driven aggregation is irreversible and redissolution usually requires the addition of trifluoroethanol to the aggregate.

For purposes of clarification, it is noted that the reversible temperature elicited aggregation, which gives rise upon standing to a dense viscoelastic phase, is called coacervation. The viscoelastic phase is called the coacervate, and the solution above the coacervate is referred to as the equilibrium solution.

Most importantly, however, in accordance with the present invention, it has now been found that cross-linked PPP, PTP and analogs thereof exhibit elastomeric force development at different temperatures spanning a range of up to about 75° C. depending upon several controllable variables. Moreover, it has been found for these cross-linked elastomers that development of near maximum elastomeric force can occur over a very narrow temperature range. Thus, by synthesizing bioelastomeric materials having varying molar amounts of the constituent pentamers and tetramers together with such units modified by hexameric repeating units, and by choosing a particular solvent to support the initial viscoelastic phase, it is now possible to rigorously control the temperature at which the obtained bioelastomer develops elastomeric force.

In general, it has been found that the process of raising the temperature to form the above elastomeric state is an inverse temperature transition resulting in the development of a regular non-random structure, unlike typical rubbers, which utilizes, as a characteristic component, hydrophobic intramolecular interactions. The regular structure is proposed to be a β-spiral, a loose water-containing helical structure with β-turns as spacers between turns of the helix which provides hydrophobic contacts between helical turns and has suspended peptide segments. These peptide segments are free to undergo large amplitude, low frequency rocking motions called librations. Consequently, a new mechanism of elasticity has now been developed called the librational entropy mechanism of elasticity.

It has now been found that the elastomeric force of these various bioelastomers develops as the regular structure thereof develops. Further, it has been found that a loss of regular structure by high temperature denaturation, results in loss of elastomeric force. Interestingly, this situation is just the reverse of that for the random-chain-network theory of elasticity, in which the more nearly random the polypentapeptide, the less the elastomeric force, and the more developed the β-turn containing structure, the greater the elastomeric force.

In the broadest sense, the present invention pertains to the development of a new entropy-based mechanism of elasticity. The mechanism therefor appears to be derived from a new class of polypeptide conformations called β-spirals wherein β-turns recur with regularity in a loose water-containing helix. The β-spiral is the result of intramolecular interturn hydrophobic interactions which form on raising the temperature in water. In the β-spiral of the elastomeric polypentapeptide of elastin, $(Val^1\text{-}Pro^2\text{-}Gly^3\text{-}Val^4\text{-}Gly^5)_n$, the type II $Pro^2\text{-}Gly^3$ β-turns function as spacers, with hydrophobic contacts, between the turns of the helix, which results in the segments of $Val^4\text{-}Gly^5\text{-}Val^1$ being suspended. Being essentially surrounded by water, the peptide moieties of the suspended segments are free to undergo large rocking motions referred to as librations which become damped on stretching. The decrease in amplitude of librations on stretching constitutes a decrease in entropy and it appears that the decrease in free energy due to the increase in entropy on returning to the relaxed state is the driving force for elastomeric retraction.

In accordance with the present invention, upon raising the temperature of the polypeptide-solvent system, such as PPP-water, for example, the hydrophobic side chains such as those of Pro and Val when dispersed in water are surrounded by water having a clathratelike structure, that is, by water that is more ordered than normal bulk water. Upon raising the temperature, an amount of this more ordered clathrate-like water surrounding the hydrophobic groups becomes less ordered bulk water as the hydrophobic chains associate to form a more ordered polypeptide. It appears that it is the optimization of intramolecular hydrophobic contact that assists the polypeptide in wrapping up into a loose helix. Adherence to the Second Law of Thermodynamics appears to be maintained by the requirement that the decrease in entropy of the polypeptide portion of the system be less than the increase in entropy of the water in the system. Since $\Delta G = 0$ at the temperature midpoint $(T_{mp})$ of a structural transition between a pair of states, then $T_{mp} = \Delta H/\Delta S$. If the entropy change, $\Delta S$, derives from the hydrophobicity of the repeating unit, as it would in the clathrate-like water mechanism, than an increase in the hydrophobicity of the repeating unit can be used to explain the decrease in $T_{mp}$, the midpoint of the inverse temperature transition. In fact, in accordance with the present invention, it has been found that a decrease in the hydrophobicity of the repeating unit results in an increase in $T_{mp}$. Conversely, an increase in the hydrophobicity of the repeating units results in a decrease in $T_{mp}$.

The above principle can be demonstrated by substituting the more hydrophobic isoleucine (Ile) for valine (Val) in the elastin polypentapeptide, $(Ile^1\text{-}Pro^2\text{-}Gly^3\text{-}Val^4\text{-}Gly^5)_n$, i.e., $Ile^1$-PPP, to produce a substituted polypentapeptide which has properties similar to PPP, except that the described transition occurs at a lower temperature. See FIGS. 1–3.

For purposes of clarity, it is noted that for the above numbered sequence and all sequences hereafter, the superscript numbering system is a sequence numbering based upon the dominant secondary structural feature of these repeating sequences which is the type II $Pro^2$-$Gly^3$ β-turn, a ten atom hydrogen bonded ring involving the C=O of residue 1 and the NH of residue 4.

The present invention also has been found to extend to the polytetrapeptide of elastin. It is recalled that this repeating unit has the formula $(Val^1-Pro^2-Gly^3-Gly^4)_n$, which also forms a β-spiral similar to PPP. However, the temperature of aggregation for PTP occurs at a higher temperature than for PPP. In essence, for both the polypentapeptide and polytetrapeptide repeating units of elastin, the present inventors have found that the temperature of the transition for the development of elastomeric force is proportional to the hydrophobicity of the repeating unit. This is shown graphically in FIG. 9. Hence, two important principles elucidated by the present invention may now be stated. First, is that elastomeric force development occurs due to an inverse temperature transition resulting in increased polypeptide order by raising the temperature. Secondly, the temperature of this transition for the development of elastomeric force is proportional to the hydrophobicity of the repeating unit in the bioelastomer.

In accordance with the present invention, analogs of both the elastin polypentapeptide PPP and the polytetrapeptide (PTP) and combinations thereof are contemplated. For example, it has been found that the temperature of transition for $Ile^1$-PPP shifts to a lower temperature by an amount calculable from the increase in hydrophibicity relative to PPP using the hydrophobicity scales shown in FIG. 9. Thus, by carefully choosing a new analog with a different repeating unit hydrophobicity, the transition temperature for the development of elastomeric force can be predictably shifted to a different temperature. In fact, by judiciously selecting various repeating units and combinations thereof, along with various solvent mixtures it is now possible to select a transition temperature from within a range of up to about 75° C., from about −25° C. to about +50° C.

As noted previously, the most striking repeating sequence of the elastin polypentapeptide is $(Val^1-Pro^2-Gly^3-Val^4-Gly^5)_n$, wherein, for example, n is 13 for chicks and 11 for pigs. The polypentapeptide is soluble in water at all proportions below 25° C. On raising the temperature above 25° C., aggregation occurs and the aggregate settles to form a dense viscoelastic phase coacervate that at 40° C. is about 38% peptide and 62% water by weight. The process of PPP coacervation, as noted, is entirely reversible. Moreover, on cross-linking, the PPP coacervate is found to be elastomeric. The coacervate concentration of PPP as well as the elastomeric γ-irradiation cross-linked PPP coacervate undergo an inverse temperature transition, which commences at 25° C. and which reaches completion near 37° C. Over the same temperature range, the elastomeric force of the cross-linked PPP coacervate increases dramatically from near zero at 20° C. to full force near 40° C. Above 40° C., the elastomeric force divided by the temperature (°K) becomes quite constant.

This indicates that the cross-linked PPP is a dominantly entropic elastomer. That is, the entropic component of the elastomeric force depends upon the decrease in numbers of low energy states accessible to the polymer on extension, whereas the internal energy component of elastomeric force results from stressing of bonds which would increase the probability of rupture of the elastomer. Interestingly enough, with the development of near maximum entropic elastomeric force upon raising the temperature from 25° C. to 37° C., it would appear that the polypentapeptide of elastin specifically evolved for warm-blooded animals. Further, it appears that this evolution occured at a relatively early stage in mammalian evolution, inasmuch as these repeating peptide sequences appear to have remained unchanged throughout the past 200 million years of mammalian evolution.

Thus, in part, the present invention is predicated upon the finding that it is possible to change the temperature of transition by modifying the PPP. In particular, it has been found that by increasing the hydrophobicity of the PPP repeating unit, the viscoelastic phase transition occurs at lower temperatures, while by decreasing the hydrophobicity of the repeating unit, this transition occurs at higher temperatures. Of course, when modifying the hydrophobicity, it is necessary to do so in a way such that elasticity is retained.

For example, modifications of the repeating pentamers have been made which destroy the molecular structure required for elasticity, such as the $Ala^1$ and $Ala^5$ analogs. The $Ala^1$ and $Ala^5$ analogs, the former decreasing and the latter increasing pentamer hydrophobicity, result in the formation of granular precipitates on raising the temperature of aqueous solutions rather than forming viscoelastic coacervates and γ-irradiation cross-linking of the $Ala^5$-PPP precipitate results in a hard material that simply breaks upon stretching. In accordance with the present discovery, it is believed that these analogs fail to produce elastomeric polymers for different but consistent reasons. First, the $Ala^1$ analog does not appear to allow for important $Val^1$ $\gamma CH_3$ ... $Pro^2$ $\delta CH_2$ intramolecular hydrophobic contacts required to form a viscoelastic coacervate. The $Ala^5$ analog appears to interfere with librational motions in the $Val^4$-$Gly^5$-$Val^1$ suspended segment of the proposed PPP molecular structure. As noted, the librations are central to the proposed librational entropy mechanism of elasticity.

By contrast, the hydrophobicity of the repeating pentamer can be easily increased by introducing a—$CH_2$—moiety, for example, in residue 1 while maintaining β-branching, that is, to utilize the $Ile^1$ analog of PPP, i.e., $(Ile^1-Pro^2-Gly^3-Val^4-Gly^5)_n$. With a greater than 50,000 molecular weight, $Ile^1$-PPP reversibly forms a viscoelastic coacervate with the onset of coacervation being at 8° C. rather than 24° C. as for unsubstituted PPP. It appears from circular dichroism data that $Ile^1$-PPP and PPP have identical conformations both before and after the transitions and that the transition to increased intramolecular order on increasing the temperature is also shifted by 15° C. or more to lower temperatures. Further, the dramatic increase in elastomeric force on raising the temperature of the γ-irradiation cross-linked coacervate is similarly shifted to a lower temperature for the $Ile^1$-PPP analog. Thus, with this analog, a coupling of temperature dependent elastomeric force development and molecular structure is demonstrated. This, of course, means that it is now possible to rationally design polypeptide elastomers that undergo transitions at different temperatures and that would function as entropic elastomers in different temperature ranges.

As noted above, by increasing the hydrophobicity of PPP, such as by substituting $Ile^1$ for $Val^1$ in the pentameric sequence of —$(VPGVG)_n$ to form —$(IPGVG)_n$, it is now possible to accomplish at least two distinct objectives.

First, it is now possible to prepare, for example, the "homopolymeric" polypentapeptide of —(IPGVG)$_n$—, i.e., Ile$^1$-PPP, which, as noted dissolves in water at 4° C., and upon raising the temperature to 8° C., exhibits aggregation. After cross-linking the coacervate by γ-irradiation, it is observed that essentially full elastomeric force is exhibited at about 25° C. for the cross-linked Ile$^1$-PPP as opposed to the 40° C. temperature required for the unsubstituted PPP. Thus, the temperature ordered transition for Ile$^1$-PPP occurs at a temperature approximately 15° C. lower than for PPP.

Secondly, it is now also possible to prepare mixed "copolymers", for example, of the polypentapeptides —X$^1$—(IPGVG)$_n$—Y$^1$—and —X$^2$—(VPGVG—)$_n$—Y$^2$—which exhibit variable and controllable transition temperatures which are in between the separate transition temperatures of PPP and Ile$^1$-PPP. Further, a great degree of control is possible inasmuch as the transition temperature obtained is directly proportional to the molar ratios of the respective pentapeptides incorporated therein.

Perhaps the most striking feature of the increased hydrophobicity PPP cross-linked analogs is that nearly full elastomeric force can be reached over a very narrow temperature range. For example, for cross-linked Ile$^1$-PPP, it is found that the elastomeric force thereof shows an abrupt increase from essentially zero at 8° C. to three-quarters of full force at 10° C., and essentially full force by 20°-25° C. Such an increase in elastomeric force over only a 2° C. temperature differential is, indeed, unprecedented and can be controlled by the percent extension in relation to swelling of the elastomer on lowering the temperature.

Although Ile$^1$-PPP is an excellent example of an increased hydrophobicity PPP analog, any PPP analog, which reduces the hydrophobicity of the repeating pentameric unit, while retaining the elasticity of the polypeptide, and without interfering with either the formation of the viscoelastic coacervate or the librational motion is within the ambit of the present invention.

For example, in addition to repeating unit sequences of —(IPGVG—)$_n$, using Ile$^1$, it is also possible to effect a variety of other substitutions. In general, a pentapeptide repeating unit of the formula:

—(R$_1$PR$_2$R$_3$G)$_n$— is within the ambit of the present invention, wherein R$_1$ is selected from the group consisting of Phe, Leu, Ile, and Val; R$_2$ is selected from the group consisting of Ala and Gly; R$_3$ is selected from the group consisting of Phe, Leu, Ile, and Val; and n is an integer from 1 to 200; and P is L-proline and G is glycine.

Notably, the above substitutions modify the hydrophobicity of the repeating unit so as to attenuate the transition temperature for near maximum elastomeric force development, of course, without destroying the elasticity of the bioelastomer.

In the above formula, it is noted that the amino acid Leu is, of course, Leucine. R$_1$, R$_2$ and R$_3$ correspond to positions 1, 3 and 4 in the numbered sequence as described herein.

Interestingly, with Phe$^1$-PPP in water, it is possible to shift the temperature of transition initiation from 25° C. for PPP to about 0° C. Furthermore, this shift can be driven to even lower temperatures by utilizing mixed solvent systems of water/ethylene glycol or water/dimethyl sulfoxide (DMSO). For example, by using the Phe$^1$-PPP/water-ethylene glycol system, a transition temperature of as low as about −25° C. can be obtained. Of course, a range of transition temperatures can be obtained between 0° C. and about −25° C. for the Phe$^1$-PPP/water-ethylene upon glycol system depending upon the amount of ethylene glycol added. It has been found that very low transition temperatures are obtained using approximately 50/50 mixtures of water/ethylene glycol.

Conversely, the maximum shift to higher transition temperatures is limited by the denaturation of the polypeptide. With the present elastomeric polypeptides, this upper limit appears to be about 50° C., with denaturation beginning above 60° C.

However, as noted previously, the present invention includes not only PPP analogs, such as Ile$^1$-PPP, Phe$^1$-PPP or Ala$^3$-PPP but all PPP analogs, and bioelastomers containing the same, which have transition temperatures, and, hence, temperatures of near maximum elastomeric force development, which are different from PPP; while retaining elasticity. Given, the present disclosure, one skilled in the art could clearly ascertain additional PPP analogs, and bioelastomers incorporating the same which meet the above criteria.

As noted above, the increased hydrophobicity analog, such as Ile$^1$-PPP may be synthesized as a "homopolymer", or a "copolymer" of —X$^2$—(VPGVG—)$_n$—Y$^2$—and —X$^1$—(IPGVG—)$_n$—Y$^1$—may be synthesized with the molar ratio of the constituent pentamers being dependent upon the desired temperature for elastomeric force development. However, in general, in such "copolymers", the —X$^1$—(IPGVG—)$_n$—Y$^1$—pentameric component is present in about 1-99% of the total pentameric molar content, while the —X$^2$—(VPGVG—)$_n$—Y$^2$—pentameric component is present in about 99-1% of the total pentameric molar content. More preferably, the —X$^1$—(IPGVG—)$_n$—Y$^1$—component is present in about 5-95% of the total pentameric molar content, while the —X$^2$—(VPGVG—)$_n$—Y$^2$—component is present in about 95-5% of the total pentameric molar content. However, any combination of relative molar amounts can be used as dictated by the desired transition temperature.

Thus, in accordance with one aspect of the present invention, bioelastomers can be prepared which contain elastomeric units comprising tetrapeptide, or pentapeptide or units thereof modified by hexapeptide repeating units and mixtures thereof, wherein said repeating units comprise amino acid residues selected from the group consisting of hydrophobic amino acid and glycine residues, wherein the repeating units exist in a conformation having a β-turn which comprises a polypentapeptide unit of the formula:

—X$^1$—(IPGVG—)$_n$—Y$^1$— wherein
 I is a peptide-forming residue of L-isoleucine;
 P is a peptide-forming residue of L-proline;
 G is a peptide-forming residue of glycine;
 V is a peptide-forming residue of L-valine; and
wherein X is PGVG, GVG, VG, G or a covalent bond; Y is IPGV, IPG, IP or I or a covalent bond; and n in both formulas is an integer from 1 to 200; or n is 0, with the proviso that X$^1$ and Y$^1$ together constitute a repeating pentapeptide unit, in an amount sufficient to adjust the development of elastomeric force of the bioelastomer to a predetermined temperature.

However, the present invention also relates, as noted above, to bioelastomers which contain elastomeric units comprising tetrapeptide, or pentapeptide or units thereof modified by hexapeptide repeating units and mixtures thereof, wherein said repeating units comprise amino acid residues selected from the group consisting of hydrophobic amino acid and glycine residues, wherein the repeating units exist in a conformation having a β-turn which comprises (A) a polypentapeptide unit of the formula:

and (B) a polypentapeptide unit of the formula:

wherein for the above formulas,
I is a peptide-forming residue of L-isoleucine;
P is a peptide-forming residue of L-proline;
G is a peptide-forming residue of glycine;
V is a peptide-forming residue of L-valine; and
wherein $X^1$ and $X^2$ are each PGVG, GVG, VG, G or a covalent bond; $Y^1$ is IPGV, IPG, IP or I or a covalent bond; $Y^2$ is VPGV, VPG, VP, V or a covalent bond; and n in both formulas an integer from 1 to 200; or n in both formulas is 0, with the proviso that $X^1$ and $Y^1$ together, and $X^2$ and $Y^2$ together constitute a repeating pentapeptide unit, in relative amounts sufficient to adjust the development of elastomeric force of the bioelastomer to a predetermined temperature.

It should be noted that bioelastomeric polypeptide chains containing either one or both of the above pentapeptide repeating units can be synthesized using any of the pentapeptide "monomers" that are permutations of the basic sequence. However, if the polymer is not synthesized using the pentapeptide "monomers", but rather is synthesized by sequential adding of amino acids to a growing peptide, such as in the case of an automatic peptide synthesizer, the designation of the repeating unit is somewhat arbitrary. For example, the peptide H-V(PGVGVPGVGVPGVGVPGVGV)P-OH can be considered to consist of any of the following repeating units and end groups: H-(VPGVG)$_4$-VP-OH, H-V-(PGVGV)$_4$-P-OH, H-VP-(GVGVP)$_4$-OH, H-VPG-(VGVPG)$_3$-VGVP-OH, or H-VPGV-(GVPGV)$_3$-GVP-OH, for example.

Furthermore, it is entirely possible and within the ambit of the presen invention that mixed repeating units such as those of the formula $-(-VPGVGIPGVG-)-_n$ can be incorporated into the bioelastomers of the present invention.

Synthesis of the elasticity promoting and modifying segments, which are incorporated into the final elastomeric polypeptide, is straightforward and easily accomplished by a peptide chemist. The resulting intermediate peptides generally have the structure, $B^1$-(repeating unit)$_n$-$B^2$, where $B^1$ and $B^2$ represent any chemically compatible end group on the amino and carboxyl ends of the molecule, respectively, and n is an integer of from 2 to about 200. Of course, when $B^1$ is —H and $B^2$ is —OH, and n is 1, the compound is either the pentapeptide H-VPGVG-OH or H-IPGVG-OH. When n is greater than 1, the compound intermediate is a polypentapeptide. The same will hold true when utilizing tetrameric repeating units in the present bioelastomers.

It should be noted that the term "hydrophobic amino acid" refers to amino acids which have appreciably hydrophobic R groups as measured on a hydrophobicity scale generated by measuring the relative solubilities of the amino acids in organic solvents. In this respect, see Arch. Biochem. Biophy, Bull and Breese, Vol. 161, 665–670 (1974). By this method, all amino acids which are more hydrophobic than glycine may be used. More specifically, preferable hydrophobic amino acids are Ala, Val, Leu, Ile and Pro.

It should also be noted that it is entirely possible that one or more amino acid residues or segments of amino acid residues not present in the normal pentapeptide or tetrapeptide sequence may be interspersed within a polypentapeptide or polytetrapeptide portion of an elastomeric polypeptide chain.

The bioelastomers of the present invention, regardless of the particular functional repeating unit incorporated therein, may have these repeating units incorporated either in the form of block or random copolymers as long as the desired shift in temperature of elastomeric force development of the bioelastomer is obtained. As noted above, by considering the transition temperatures and temperatures of elastomeric force development for two PPP or PTP analogs, or even for a PPP analog and a PTP analog, it is possible to attain a desired intermediate transition temperature and temperature of elastomeric force development by directly correlating the molar ratios of each analog component therewith. For example, a 50/50 molar ratio of two analog components would give rise to a bioelastomer "copolymer" having a transition temperature and temperature of elastomeric force development approximately in between those of the analog components.

Additionally, it is also noted that the elastomeric units used in conjunction with all aspects of the present invention, i.e., whether the repeating unit is PPP, PTP or analogs thereof, may also comprise those described in U.S. Pat. Nos. 4,187,852; 4,474,851; 4,500,700, and 4,589,882 and U.S. patent applications 533,670, 793,225 and 853,212 all of which patents and patent applications are incorporated herein in their entirety.

The aspect of the present invention with respect to PPP and analogs thereof will now be illustrated by Examples, which are provided only for the purpose of illustration and are not intended to limit the present invention.

EXAMPLES

Peptide Synthesis

The synthesis of Ile$^1$-PPP was carried out by the classical solution methods as shown in Scheme I.

In the following Examples, the following abbreviations will be used: Boc, tert-butyloxycarbonyl; Bzl, benzyl; DMF, dimethylformamide; DMSO, dimethylsulfoxide; EDCI, 1-(3-dimethylaminopropyl)-3-ethylcarbodiimide; HOBt, 1-hydroxybenzotriazole; IBCF, isobutylchloroformate; NMM, N-methylmorpholine; ONp, p-nitrophenbylester; TFA, trifluoroacetic acid; PPP, (VPGVG)$_n$; Ile$^1$-PPP, (IPGVG)$_n$; V, valine; I, isoleucine; P, proline; G, glycine.

Scheme I
Synthesis of H—(Gly—Val—Gly—Ile—Pro)$_n$—OH

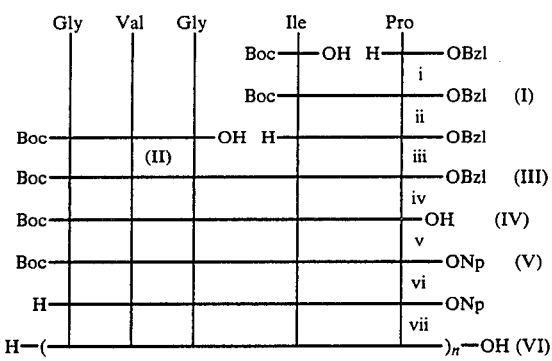

i IBCF/HOBt;
ii HCl/Dioxane;
iii EDCI/HOBt;
iv H$_2$—Pd/C;
v Bis(p-nitrophenyl)carbonate;
vi TFA;
vii DMSO—NMM The sequence of the starting pentamer for polymerization is preferably Gly-Val-Gly-Ile-Pro rather than Ile-Pro-Gly-Val-Gly, because the permutation with Pro as the C-terminal amino acid produces high molecular weight polymers in better yields. The approach to the synthesis entailed coupling the tripeptide Boc-GVG-OH (II) with H-IP-OBzl, each in turn being synthesized by the mixed anhydride methodology of J. R. Vaughan et al, *J. Am. Chem. Soc.*, 89, 5012 (1967). The possible formation of the urethane as a by-product during the reaction of Boc-Ile-OH with H-Pro-OBzl by the mixed anhydride method was avoided by carrying out the reaction in the presence of HOBt. The dipeptide was also prepared using EDCI for confirmation of the product. The pentapeptide benzylester (III) was hydrogenated to the free acid (IV) which was further converted to the p-nitrophenylester (V) on reacting with bis(p-nitrophenyl)carbonate. On removing the Boc-group, a one molar solution of the active ester in DMSO was polymerized in the presence of 1.6 equiv. of NMM. The polypeptide was dialyzed against water using a 50,000 dalton cut-off dialysis tubing and lyophilized. The purity of the intermediate and final products was checked by carbon-13 nuclear magnetic resonance, elemental analyses and thin layer chromatography (TLC).

Elemental analyses were carried out by Mic Anal, Tuscon, Ariz. All amino acids are of L-configuration except for glycine. Boc-amino acids were purchased from Bachem, Inc., Torrance, Calif. HOBt was obtained from Aldrich Chemical Co., Milwaukee, Wis. TLC was performed on silica gel plates purchased from Whatman, Inc., Clifton, N.J. in the following solvent systems: $R_f^1$, CHCl$_3$ (C):CH$_3$OH(M):CH$_3$COOH(A), 95:5:3; $R_f^2$, CMA (85:15:3); $R_f^3$, CMA (75:25:3); $R_f^4$, CM (5:1). Melting points were determined with a Thomas Hoover melting point apparatus and are uncorrected.

Boc-Ile-Pro-OBzl (mixed anhydride method) (I): Boc-Ile-OH (12.01 g, 0.05 mole) in DMF (50 ml) was cooled to 0° C. and NMM (5.49 ml) was added. After cooling the solution to −15° C. isobutylchloroformate (6.48 ml) was added slowly while maintaining the temperature at −15° C. and stirred for 10 minutes at which time HOBt (7.65 g) was added and stirring was continued for additional 10 minutes. A pre-cooled solution of HCl-H-Pro-OBzl (12.09 g, 0.05 mole) in DMF (50 ml) and NMM (5.49 ml) was added to the above solution and the completeness of the reaction was followed by TLC. The reaction mixture was poured into a cold saturated NaHCO$_3$ solution and stirred for one hour. The peptide was extracted into CHCl$_3$ and washed with acid and base (0.5 N NaOH to remove HOBt), and on evaporating the solvent the product was obtained as an oil in 92% yield. $R_f^1$, 0.65. Anal. Calcd. for C$_{23}$H$_{34}$N$_2$O$_5$: C 66.00, H 9.19, N 6.69%. Found: C 65.58, H 8.28, N 7.13%.

Boc-Ile-Pro-OBzl (using EDCI): Boc-Ile-OH (7.20 g, 0.03 mole) and HOBt (5.05 g, 0.033 mole) in DMF (30 ml) was cooled to −15° C. and EDCI (6.32 g, 0.033 mole) was added. After stirring for 20 minutes, a pre-cooled solution of HCl-H-Pro-OBzl (7.25 g, 0103 mole) in DMF (30 ml) and NMM (3.3 ml) was added and stirred overnight at room temperature. After evaporating DMF, the residue was taken into CHCl$_3$ and extracted with 20% citric acid and 0.5N NaOH. The solvent was removed and the product was obtained as an oil in almost quantitative yield which was identical to the product obtained by the mixed anhydride method.

Boc-Gly-Val-Gly-Ile-Pro-OBzl (III): Boc-GVG-OH (II) (20) (5.6 g, 0.017 mole) was coupled with H-Ile-Pro-OBzl (6.7 g, 0.019 mole) (obtained by deblocking I with HCl/Dioxane) in the presence of EDCI (3.65 g, 0.019 mole) and HOBt (2.9 g, 0.019 mole) and the product was worked up as described above to obtain 8.8 g of III (yield: 82.4%), m.p. 107°–108° C. (decomp.) $R_f^1$, 0.44; $R_f^2$, 0.75. Anal. calcd. for C$_{32}$H$_{49}$N$_5$O$_{10}$: C 60.83, H 7.81, N 11.08%. Found: C 61.12, H 8.06, N 11.06%.

Boc-Gly-Val-Gly-Ile-Pro-OH (IV): III (7.8 g, 0.0123 mole) was taken in acetic acid (80 ml) and hydrogenated in the presence of 10% Pd-C (1 g) at 40 psi. After filtering the catalyst with the aid of celite, the solvent was removed under reduced pressure, triturated with ether, filtered, washed with ether then pet. ether and dried to obtain 6.5 g of the product (yield: 97.3%), m.p. shrinks at 127° C. and decomp. at 145° C. $R_f^3$, 0.24; $R_f^4$, 0.11. Anal. Calcd. for C$_{25}$H$_{43}$N$_5$O$_{10}$.1/2H$_2$O: C 54.52, H 8.05, N 12.71%. Found: C 54.32, H 8.02, N 12.59%.

Boc-Gly-Val-Gly-Ile-Pro-ONp (V): IV (5.41 g, 0.01 mole) in pyridine (40 ml) was reacted with bis(p-nitrophenyl)carbonate (4.56 g, 0.015 mole) following the completeness of the reaction by TLC. Pyridine was removed; the residue was taken into CHCl$_3$ and extracted with acid and base. The p-nitrophenyl ester obtained was chromatographed over a silica gel (200–400 mesh) column. After initial washing with CHCl$_3$, 4.8 g of V was obtained when eluted with 35% acetone in CHCl$_3$ (yield: 71.4%), m.p. 97°–100° C. $R_f^2$, 0.72; $R_f^4$, 0.75; Anal. Calcd. for C$_{31}$H$_{46}$N$_6$O$_{12}$.2H$_2$O: C 53.28, H 7.21, N 12.02%. Found: C 53.76, H 6.83, N 12.01%.

H-(Gly-Val-Gly-Ile-Pro)$_n$-OH(VI): The Boc-group was removed from V (3.8 g, 0.0057 mole) by reacting with TFA (35 ml) for 45 min. TFA was removed under reduced pressure, triturated with ether, filtered, washed with ether, pet. ether and dried. The TFA salt (3.3 g, 0.0049 mole) in DMSO (4.9 ml) was stirred for 14 days in the presence of NMM (0.86 ml, 0.0078 mole). After diluting with water in the cold, the polypeptide was dialyzed using a 50 kD cut-off dialysis tubing changing the water daily for 15 days. The retentate was lyophilized to obtain 1.81 g of the Ile$^1$-polypentapeptide (yield: 88%). The carbon-13 NMR spectrum is presented in FIG. 1 along with that of the regular polypentapeptide for comparison.

Temperature Profiles for Coacervation

The temperature dependence for aggregation of the polypentapeptide is followed as the development of turbidity at 300 nm using a Cary 14 spectrophotometer. The sample cell is placed within a chamber vibrating at 300 Hz in order to facilitate equilibrium and to keep the aggregates from settling. The scan rate is 30° C./hour and the temperature was controlled with a Neslab ETP-3 programmer and monitored with an Omega 199A thermocouple monitor placed at the cell. The turbidity as a function of temperature provides a temperature profile for coacervation which is found to be concentration dependent. As the concentration is raised, the profile shifts to lower temperatures until further increases in concentration cause no further lowering of the temperature for aggregation. This defines the high concentration limit. The temperature for the onset of coacervation at the high concentration limit coincides with the temperature for the onset of the transition within the coacervate itself, even when there is no appreciable change in water content of the coacervate. The temperature for the midpoint of the temperature profile for the high concentration limit has been shown to correlate with the molecular weight of the polypentapeptide. When the midpoint is 25° C. for the PPP, the molecular weight is close to 100,000 daltons as calibrated by dialysis. For the Ile$^1$-PPP with a midpoint of 9° C., the molecular weight is greater than 50,000 daltons, as the synthetic polypeptide was retained by a 50,000 daltons dialysis membrane. The dialysis was carried out at 4° C. where the Ile$^1$-PPP is in solution.

Circular Dichroism Measurements

The circular dichroism studies were carried out on a Cary 60 spectropolarimeter equipped with a Model 6001 CD accessory modified for 330 Hz modulation of the left and right circularly polarized light. A concentration of 0.025 mg Ile$^1$-PPP/ml of doubly distilled water was characterized in a 10 mm path length cell. The low concentration was used to keep the size of the aggregate sufficiently small as not to cause light scattering distortions of the CD spectra. Even at this low concentration with this more hydrophobic polypentapeptide, above 35° C. the size of the aggregates was sufficient to cause particulate distortions as was apparent with the red shifting and dampening of the long wavelength negative band. The temperature was controlled and monitored from the cell as for the temperature profiles for coacervation.

Formation of the Elastomeric Matrix

In preparation for γ-irradiation cross-linking (the means of forming the elastomeric matrix), 130 milligrams of peptide Ile$^1$-PPP were dissolved in 220 milligrams of water in a cryotube. The sample was then shear oriented at 0° C. in a previously described pestle-cryotube arrangement. Gamma-irradiation was carried out at the Auburn University Nuclear Science Center at a dose rate of approximately 8,000 Roentgen/min and for sufficient time to achieve a $20 \times 10^6$ radiation absorbed dose (20 Mrad).

Thermoelasticity Studies

Thermoelasticity studies were carried out on a stress-stain instrument built in this Laboratory. The sample is mounted in two Delrin clamps. The top clamp is attached to a Statham UTC strain-gauge and the assembly is fixed. The bottom clamp is attached to a moving platform driven by a variable speed motor. Both clamps are enclosed in a thermostated water jacket. An inner chamber contains the solvent in which the elastomer is immersed which in this case is doubly distilled water. The sample was fixed in the top clamp and equilibrated in water at 60° C. for about an hour. The strain-gauge signal conditioner was balanced for zero force and the bottom clamp was attached to the sample. The sample was left to set overnight at room temperature. The bottom clamp was then adjusted for zero force and the distance between the clamps was measured. The elastomer was elongated to 40% extension at 5° C. and elastomeric force was then determined as a function of temperature. Equilibrium time to achieve constant force at a given temperature was typically twenty-four hours. Force measurements were made in 2° C. increments through the sharp rise in force and 5° C. increments at higher temperatures.

RESULTS

Temperature Profiles for Coacervation

The Ile$^1$-PPP can be dissolved in water on standing below 8° C. On raising the temperature of the solution above 8° C., the solution becomes cloudy; on standing at the elevated temperature settling occurs and a viscoelastic phase forms in the bottom of the vial; on placing the vial in an ice bath the cloudiness immediately clears and the viscoelastic phase readily dissolves. Thus the Ile$^1$-PPP coaceravates when dissolved in water. The temperature profiles for coacervation (turbidity profiles) are shown in FIG. 2A for different concentrations. As the concentration is raised, the temperature profile shifts to lower temperature. At 40 mg/ml, the high concentration limit (i.e, the lower concentration for which further increases in concentration cause no further lowering of the temperature for the onset of aggregation), the midpoint for the temperature profile for coacervation of Ile$^1$-PPP is 9° C.

Included for comparison in FIG. 2A are the data for the PPP of elastin demonstrating the temperature profile midpoint for the high concentration limit to be 25° C. The simple addition of a $CH_2$ moiety to the 409 dalton repeating unit causes the onset of aggregation to shift to lower temperatures by 16° C. Observing that curve f (0.1 mg Ile$^1$-PPP/ml) and curve k (1.0 mg PPP/ml) are comparable with respect to the high concentration limits for each high molecular weight polymer suggests that the size of the aggregate for Ile$^1$-PPP is greater for a given concentration than it is for a comparable concentration of PPP. This will be relevant to comparisons made in the circular dichroism data.

Circular Dichroism

Figure 3:
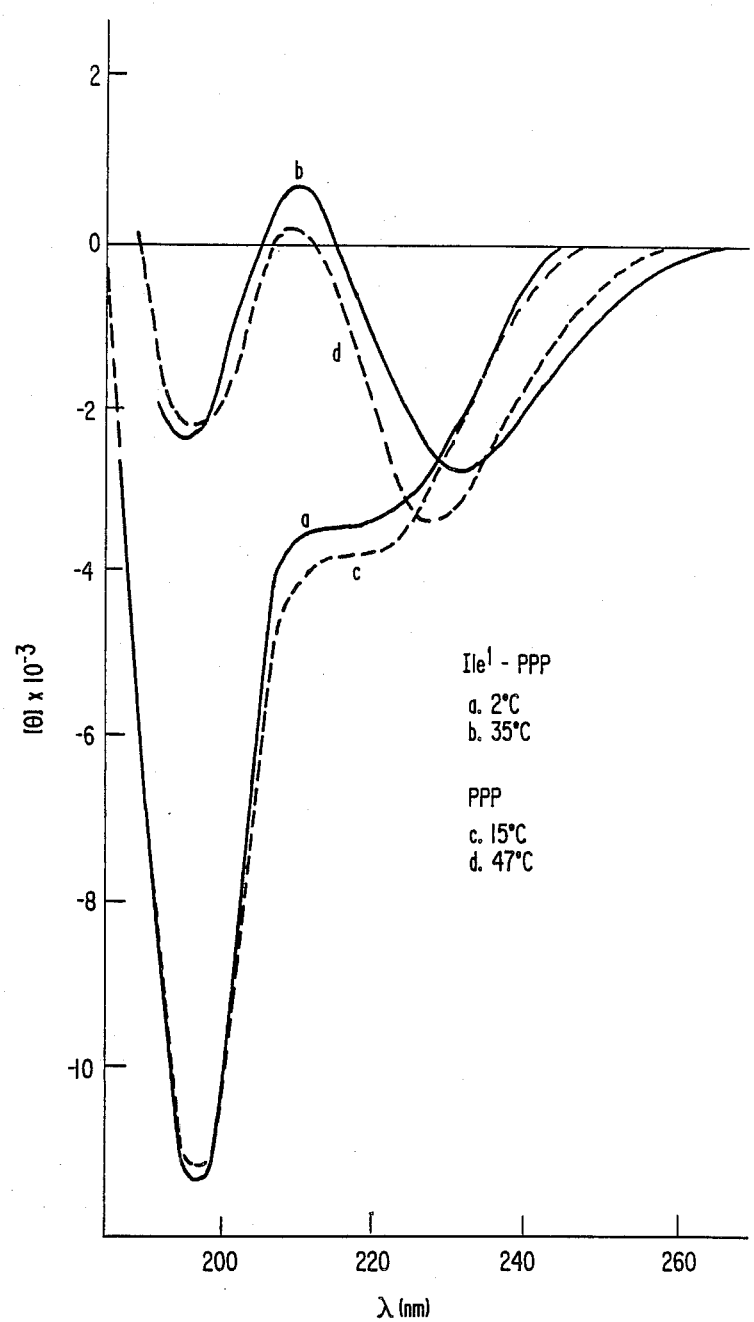

In FIG. 3 are the circular dichroism curves for Ile$^1$-PPP in water (0.025 mg/ml) at 2° C. and at 35° C. The low concentration was chosen in order that the size of the aggregate formed on association at 35° C. would have limited particulate distortions in the CD spectrum. At low temperature there is a large negative band near 195 nm. Such a negative band is characteristic of disordered proteins and polypeptides, though a standard value for this negative peak for complete disorder is $-4 \times 10^4$ rather than the observed value of $-1.2 \times 10^4$. Also the negative band near 220 nm, rather than zero ellipticity or a positive band which are taken as indicative of complete disorder, suggests elements of order at low temperature. The decrease in intensity of the negative CD band near 195 nm on raising the temperature of Ile[1]-PPP in water indicates an increase in intramolecular order on raising the temperature, that is, there is an inverse temperature transition in an aqueous system. This indicates that hydrophobic interactions are developing as the ordered state develops. The intramolecular increase in order begins just above 0° C. and is complete by about 30° C. for a concentration of 0.025 mg/ml. As is apparent from the data in FIG. 2A, the transition would have been complete at a lower temperature (the transition would have been sharper) if the CD data could have been obtained at higher concentration without significant particulate distortion. Shown for comparison in FIG. 2B is the value of $[\theta]_{197}$ as a function of temperature for PPP in water (2.3 mg/ml) where the transition is observed to be shifted to higher temperature by about 15° C. In FIG. 3 again for comparison are the CD spectra for PPP (0.023 mg/ml) at 15° C. below the onset temperature for the transition and at 47° C. where the transition is largely complete for this dilute concentration. It is apparent that Ile[1]-PPP and PPP have essentially identical conformations below the onset temperature for the transition and that they have essentially identical conformations after the transition is mostly completed. Thus while maintaining essentially identical conformations, which is assisted by the retention of β-branching, the addition of a $CH_2$ moiety lowers the transition toward increased order by about 15° C.

Characterization of Elasticity

The elastic (Young's) modulus determined for 20 MRAD cross-linked Ile[1]-PPP coacervate was $4 \times 10^5$ dynes/cm[2] which is within the range of values obtained for 20 Mrad cross-linked PPP. The range of values is due to variable vacuolization occurring during γ-irradiation which makes difficult accurate measurement of cross-sectional area. It should be appreciated, however, that γ-irradiation causes no detectable polymer breakdown when measured by carbon-13 and nitrogen-15 NMR.

The temperature dependence of elastomeric force is given in FIG. 2C for an elastomeric band of Ile[1]-PPP at 40% elongation. A near zero elastomeric force is measured at 8° C.; on raising the temperature there is a dramatic, an abrupt increase in elastomeric force. Full force is reached by 25° C. and becomes essentially constant with further increases in temperature. Included in FIG. 2C, again for comparison, is the data for 20 MRAD cross-linked PPP coacervate at 60% extension. There is similarly a dramatic rise in elastomeric force with increase in temperature but this curve is displaced about 15° C. to higher temperatures. Thus the results contained in FIG. 2 demonstrate with three different physical methods that the addition of a $CH_2$ moiety (the replacement of Val by Ile) shifts the transition to lower temperatures by 15° C. without changing the conformation of the polypentapeptide before and after the transition. While the previously reported data on the naturally occuring PPP of elastin demonstrate a correlation of increased structural order with increased elastomeric force, the Ile[1]-PPP data with the transition shifted by 15° C. appear to confirm an obligatory coupling of increased order with increased elastomeric force.

In fact, the correlation of increased order with increased elastomeric force is seen with the PPP. When the transition is shifted to lower temperatures, as in Ile[1]-PPP, the development of elastomeric force faithfully shifts to lower temperatures. There appears in such elastomeric polypeptides to be a strict coupling between increasing order and increasing elatomeric force; and the molecular structure provides an understanding as to how this can occur. The similar conformations of PPP and Ile[1]-PPP (see FIG. 3) and the similar elastic moduli for the two polymers indicate that these do not appear to be factors in the evolutionary retention of $(VPGVG)_n$. What is now clear is that even the subtle addition of a-$CH_2$-moiety, for example, while having little effect on the stereochemistry of rather nonexacting, nonrestricting hydrophobic associations, has a significant effect on the thermodynamics. The larger clathrate-like cage of water surrounding the Ile side chain provides a greater ΔS as the more-ordered water surrounding the side chain becomes less ordered bulk water such that in the transition ΔH=TΔS at a lower temperature. By means of calorimetry, the ΔH for PPP has been estimated at 5 to 6 cal/gram which is approximately 2 kcal/mole of pentamers. Thus, the increase in entropy change need only be about 5% to cause the temperature of the transition to decrease about 15° C. from 298° K. to 283° K. Utilizing known hydrophobicity scales for amino acids, the hydrophobicities given in a free energy of transfer scale of kcal/mole, are −4.10 for VPGVG and −5.38 for IPGVG. While the extent of the hydrophobicity that is utilized is expected to depend on the stereochemistry of the more-ordered polypeptide state, it would appear that not all of the total potential effect is actually realized.

In accordance with another aspect of the present invention, it has also now been found that the abovedescribed hydrophobic effect upon transition temperatures is also supported by the elastin polytetrapeptide, $(Val^1-Pro^2-Gly^3-Gly^4)_n$. That is, it has also been discovered that high molecular weight PTP undergoes a reversible temperature elicited aggregation with an onset of aggregation at 48° C., rather than 24° C. as for high molecular weight PPP.

However, it has also been found that the inverse temperature transition for PTP is only complete at about 70° C. Moreover, this high temperature of transition appears to be explained by considering the lower hydrophobicity of PTP as compared to PPP.

For example, utilizing the Bull-Breese hydrophobicity scales with the hydrophobicity of the Gly residue taken as zero, the free energy of transfer for the pentamer, VPGVG, would be −4100 cal/mole whereas that of the tetramer, VPGG, would be −2540 cal/mole. Thus, if hydrophobicity of the repeating unit is the determining factor, then the inverse temperature transition for the PTP would be at a higher temperature than that of the PPP. Furthermore if the inverse temperature transition (the increase in intramolecular order) is required for the development of elastomeric force, then the temperature dependence of elastomeric force of the PTP matrix would be expected to show a similar shift to higher temperature relative to that of the PPP matrix.

This inverse temperature transition is actually centered at near 50° C. for PTP, shifted some 25° C. higher than that of PPP. For Ile[1]-PTP, it is shifted some 30° C. lower in temperature than that of PTP. Also, it has been found that the development of elastomeric force upon raising the temperature is similarly shifted about 25° C.

higher for the PTP matrix (20 Mrad cross-linked) as compared to the PPP matrix (20 Mrad cross-linked).

Accordingly, in view of the above, it is now possible, by selecting the appropriate combination of PTP and PPP matrices or analogs thereof of the present invention to shift the transition temperature of a bioelastomer containing elastin PTP, PPP and analogs thereof and PHP over a range of about 75° C. Furthermore, whereever this transition would occur in the range of about −25° C. for Phe[1]-PPP in water/ethylene glycol or about 50° C. for PTP, in water, for example, there is a large change in elastomeric force which accompanies a relatively small change in temperature.

Thus, it is now possible to provide bioelastomers having incorporated therein repeating units having decreased hydrophobicity, such as —(VPGG)$_n$—.

In particular, in accordance with the present invention, is also provided a bioelastomer containing elastomeric units comprising tetrapeptide, or pentapeptide or units thereof modified by hexapeptide repeating units and mixtures thereof, wherein the repeating units comprise amino acid residues selected from the group consisting of hydrophobic amino acid and glycine residues, wherein said repeating units exist in a conformation having a β-turn which comprises a tetrapeptide of the formula:

—X$^3$—(VPGG)$_n$—Y$^3$— wherein

X$^3$ is PGG, GG, G or a covalent bond;
Y$^3$ is VPG, VP, V or a covalent bond; and
V is a peptide-producing residue of L-valine;
P is a peptide-producing residue of L-proline; and
G is a peptide-producing residue of glycine;

and n is an integer from 1 to 200, or n is 0, with the proviso that X$^3$ and Y$^3$ together constitute a repeating tetrameric unit in an amount sufficient to adjust the development of elastomeric force of the bioelastomer to a predetermined temperature.

Moreover, the present invention also further provides a bioelastomer containing elastomeric units comprising tetrapeptide, or pentapeptide or units thereof modified by hexapeptide repeating units and mixtures thereof, wherein the repeating unit comprises amino acid residues selected from the group consisting of hydrophobic amino acid and glycine residues, wherein said repeating units exist in a conformation having a β-turn which comprises (A) a polypentapeptide of the formula:

—X$^1$—(IPGVG)$_n$—Y$^1$— wherein X$^1$, Y$^1$, P, G, I, V and n are as defined above; and (B) a polypentapeptide of the formula:

—X$^2$—(VPGVG)$_n$—Y$^2$— wherein X$^2$, Y$^2$, P, G, V and n are as defined above; or (C) a polytetrapeptide of the formula:

—X$^3$—(VPGG)$_n$—Y$^3$— wherein X$^3$, Y$^3$, P, G, V and n are as defined above in relative amounts sufficient to adjust the development of elastomeric force of said bioelastomer to a predetermined temperature.

In accordance with the present invention are also provided PTP analogs, such as Ile[1]-PTP, which are analogous to the various PPP analogs described above. In fact, any PTP analog can be used in the preparation of the present bioelastomers which suffices to attenuate the hydrophobicity of the functional repeating unit, such as —(IPGG)—$_n$, while retaining the elasticity of the bioelastomer. Accordingly, in view of the principles set out above, one skilled in the art would, in view of this disclosure, be able to ascertain other PTP analogs which can be used advantageously in accordance with the present invention.

Thus, in accordance with the present invention is also provided a bioelastomer containing elastomeric units comprising tetrapeptide, or pentapeptide or units thereof modified by hexapeptide repeating units and mixtures thereof, wherein the repeating units comprise hydrophobic amino acid and glycine residues, wherein the repeating units exist in a conformation having a β-turn which comprises a tetrapeptide of the formula:

—X$^4$—(IPGG)$_n$Y$^4$— wherein

X$^4$ is PGG, GG, G or a covalent bond;
Y$^4$ is IPG, IP, I or a covalent bond; and
I is a peptide-producing residue of L-isoleucine;
P is a peptide-producing residue of L-proline; and
G is a peptide-producing residue of glycine; and n is an integer from 1 to 200, or n is 0, with the proviso that X$^4$ and Y$^4$ together constitute a repeating tetrameric unit, in an amount sufficient to adjust the temperature of which the elastomeric force of the bioelastomer develops.

Of course, also within the ambit of the present invention are bioelastomers having the above-recited structural features, but which have any combination of the repeating units —(IPGVG)—$_n$, —(VPGVG)—$_n$, —(VPGG)—$_n$, —(IPGG)—$_n$ or other analogs thereof, such as Ala[3]-PPP or Phe[1]-PPP.

In fact, the present invention includes, in general, all bioelastomers containing elastomeric units comprising tetrapeptide, or pentapeptide or units thereof modified by hexapeptide repeating units and mixtures thereof, wherein the repeating units comprise hydrophobic amino acid residues and glycine residues, wherein the repeating units exist in a conformation having a β-turn which comprises a tetrapeptide or pentapeptide unit or repeating unit thereof, in an amount sufficient to adjust the development of elastomeric force of said bioelastomer to a predetermined temperature, with the proviso that the elasticity of the bioelastomer is retained.

However, in order to clarify the various aspects of the present invention relating to PTP, the following Examples and discussion are provided. Of course, the Examples are for purposes of illustration only and are not intended to limit the present invention.

EXAMPLES

Peptide Synthesis

General Approach: The synthesis of polytetrapeptide, (VPGG)$_n$, can be achieved using any of the following permutations as the starting tetramer unit: Val-Pro-Gly-Gly, Gly-Val-Pro-Gly, Gly-Gly-Val-Pro, or Pro-Gly-Gly-Val. The first sequence (VPGG) was used in this laboratory both with the pentachlorophenyl ester (OPcp) activation and with the p-nitrophenyl ester (ONp) activation methods, and the latter method yielded polymer of significantly higher molecular weight. The sequence (GVPG) was utilized with —OPcp activation but no mention was made about the size of the polymer. In synthesizing the polypentapeptide, (VPGVG)$_n$, using different permutations of the pentamer unit with different activating groups for polymerization, it was observed that the pentamer having Pro as the C-terminal amino acid and —Onp for activation gave high molecular weight polymers. Similar results have been experienced in the case of the preparation of polyhexapeptide, (VAPGVG)$_n$. Hence, a similar approach was determined to be reasonable in the case of PTP also, i.e., sequence (GGVP) with —ONp activation. For comparison, H—VPGG—ONp, H—GV-PG—ONp and H—GGVP—ONp were all tried for polymerization. As expected, the latter tetramer sequence gave a very high molecular weight polymer when determined by the TPτ studies and here is described the synthesis of this latter material as shown in the Scheme II. The sequence (PGGV) was not attempted because it has an optically active and bulky amino acid, Val, at its C-terminal.

Scheme II
Synthesis of H—(Gly—Gly—Val—Pro)$_n$—OH

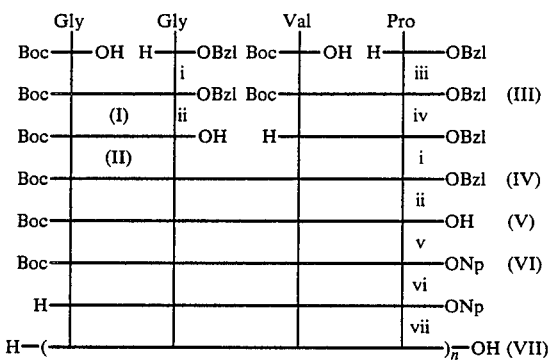

i EDCI—HOBt;
ii H$_2$—Pd/C;
iii IBCF—HOBt;
iv HCl/Dioxane
v Bis(p-nitrophenyl)carbonate;
vi TFA;
vii DMSO—NMM Boc-GG-OBzl (I) was prepared using EDCI for coupling and was hydrogenated to give the acid (II). Boc-VP-OBzl (III) was synthesized by the mixed anhydride method in the presence of HOBt, deblocked, and coupled with II using EDCI-HOBt to obtain Boc-GGVP-OBzl (IV). After hydrogenating to the acid, V, it was converted to —ONp (VI) by reacting with bis(p-nitrophenyl)carbonate. After removing the Boc-group, the active ester was polymerized, dialyzed against water using a 50,000 molecular weight cut-off dialysis tubing and lyophilized. The intermediate and the final products were checked by carbon-13 nuclear magnetic resonance, thin-layer chromatography (TLC) and elemental analyses.

Details of Syntheses: Valine and Proline are of L.configuration. Boc-amino acids were purchased from Bachem, Inc., Torrance, Calif. HOBt was obtained from Aldrich Chemical Co., Milwaukee, Wis., and Bio-sil silica gel (200–400 mesh) was purchased from Bio-Rad Laboratories, Richmond, Calif. TLC plates were obtained from Whatman, Inc., Clifton, N.J. and the following solvent systems were used for determining the homogeneity of the products: $R_f^1$, CHCl$_3$(C):MeOH (M):CH$_3$COOH (A), 95:5:3; $R_f^2$, CMA (85:15:3); $R_f^3$, CMA (75:25:3); $R_f^4$, CM (5:1). Elemental analyses were carried out by Mic Anal, Tuscon, Ariz. Melting points were determined with a Thomas Hoover melting point apparatus and are uncorrected.

Boc-Gly-Gly-OBzl (I): Boc-Gly-OH (17.52 g, 0.1 mole) in a mixture of CHCl$_3$ (50 ml) and acetonitrile (50 ml) was cooled to −15° C. and EDCI (19.17 g, 0.1 mole) was added and stirred for 20 minutes. To this, a pre-cooled solution of H-Gly-OBzl.tosylate (37.1 g, 0.11 mole), NMM (12.09 ml, 0.11 mole) in CHCl$_3$(100 ml) was added and stirred overnight at room temperature. After removing the solvent, the residue was taken in CHCl$_3$ and extracted with acid and base. Chloroform was removed under reduced pressure, triturated with pet. ether, filtered, washed with pet. ether and dried to obtain 30.2 g of I (yield: 93.7%), m.p. 82°–83° C. $R_f^2$, 0.52; $R_f^4$, 0.82. Anal. Calcd. for C$_{16}$H$_{22}$N$_2$O$_5$: C, 59.61; H, 6.88; N, 8.69%. Found: C, 59.43; H, 6.88; N, 8.35%.

Boc-Gly-Gly-OH (II): I (10 g, 0.31 mole) in acetic acid (100 ml) was hydrogenated at 40 psi in the presence of 10% Pd-C catalyst (1 g). The catalyst was filtered with the aid of celite and solvent removed under reduced pressure. The residue was triturated with EtOAC, filtered, washed with EtOAC, pet. ether an dried to yield 6.3 g of II (yield: 87.5%), m.p. 118°–120° C. (decomp.). $R_f^2$, 0.28; $R_f^3$, 0.44. Anal. Calcd. for C$_9$H$_{16}$N$_2$O$_5$.H$_2$O: C, 43.19; H, 7.25; N, 11.19%. Found: C, 43.53; H, 7.40; N 10.90%.

Boc-Gly-Gly-Val-Pro-OBzl (IV): III (6.0 g, 0.0148 mole) (39) was deblocked with HCl/Dioxane and solvent removed under reduced pressure. The residue was triturated with ether, filtered, washed with ether, then pet. ether and dried. A very hygroscopic material was obtained (4.2 g, 0.0123 mole) which was coupled in DMF with II (2.86 g, 0.0123 mole) in the presence of 10% excess of EDCI (2.60 g) and HOBt (2.07 g). The reaction was worked up as described for I to obtain IV as a white foam in a quantitative yield, no sharp m.p. 54°–62° C. $R_f^2$, 0.42; $R_f^2$, 0.74. Anal. Calcd. for C$_{26}$H$_{38}$N$_4$O$_7$; C, 60.21; H, 7.38; N, 10.80%. Found: C, 60.0; H, 7.46; N, 10.81%.

Boc-Gly-Gly-Val-Pro-OH (V): IV (6.2 g, 0.012 mole) in acetic acid was hydrogenated and worked up as for II to obtain V quantitatively, no sharp m.p. 74°–83° C. $R_f^3$, 0.25; $R_f^4$, 0.15. Anal. Calcd. for C$_{19}$H$_{32}$N$_4$O$_7$: C, 51.10; H, 7.67; N, 12.54%. Found: C, 51.28: H, 7.50N, 12.38%.

Boc-Gly-Gly-Val-Pro-ONp (VI): V (5.3 g, 0.0123 mole) in pyridine (30 ml) was reacted with bis(p-nitrophenyl)carbonate (5.64 g, 0.0185 mole). After removing the solvent, the residue was taken in CHCl$_3$ and extracted with acid and base. The peptide was chromatographed over a silica-gel column and eluted with 35% acetane in CHCl$_3$ after initially eluting with CHCl$_3$, to obtain 4.7 g of VI (yield: 69.2%), no sharp m.p. 74°–79° C. $R_f^2$, 0.76; $R_f^4$, 0.75. Anal. Calcd. for C$_{25}$H$_{35}$N$_5$O$_9$.½ H$_2$O: C, 53.75; H, 6.49; N, 12.53%. Found: C, 53.69; H, 6.44; N, 12.34%.

H-(Gly-Gly-Val-Pro)$_n$-OH (VII): VI (4.5 g, 0.0082 mole) in CHCl$_3$ (20 ml) was treated with TFA (35 ml) for 30 minutes and solvent removed under reduced pressure. The residue was triturated with ether, filtered, washed with ether, then with pet. ether and dried. The TFA salt (3.9 g, 0.0069 mole) in DMSO (7.6 ml) and NMM (1.22 ml, 1.6 equiv) was stirred for 14 days. After diluting with cold water, the polymer was dialyzed in a 50 kD cut-off dialysis tubing, changing water daily for 15 days, and the retentate was lyophilyzed to yield 1.65 g of the polytetrapeptide (yield: 77%). The carbon-13 NMR spectrum of the polymer is given in FIG. 5. The assignments are all indicated and there are no extraneous peaks thereby verifying the synthesis.

Temperature Profiles for Coacervation

Polypeptide coacervation in water is reversible aggregation to form a new phase with a distinct composition. Association occurs on raising the temperature, disassociation on lowering the temperature. The process of coacervation was followed by monitoring the turbidity as a function of temperature using a Cary 14 spectrophotometer set at 300 nm, a Neslab ETP-3 temperature programmer with a 30° C./hour scan rate and an Omega 199A thermocouple monitor. The sample cell was placed in a vibrating chamber (300 Hz) to keep the aggregates from settling and to facilitate equilibrium. The temperature profiles for coacervation are concentration dependent. Dilution from a high concentration, after the high concentration limit is reached (approximately 40 mg/ml for high molecular weight elastomeric polypeptides), results in a shift of the turbidity profile to higher temperature.

Circular Dichroism Measurements

A Cary 60 spectropolarimeter equipped with a Model 6001 circular dichroism accessory with 330 Hz modulation of the left and right circular polarized beams was used to determine the circular dichroism patterns of 5 mg PTP in one ml of deionized-distilled (quartz immersion heater) water. Because of the smaller size or the relative transparency of the PTP aggregates (as with the cross-linked PTP matrix with a relatively small change in refractive index between solution and matrix) when compared to that of the PPP system, it was possible to use the 5 mg/ml concentration for the CD studies without being compromised by light scattering (particulate) distortions of the CD spectra. This is apparent from monitoring the negative band near 220 nm which becomes damped and red-shifted as the particulate distortions become significant.

Preparation of the Cross-linked PTP Matrix

The PTP was prepared for γ-irradiation crosslinking by dissolving 130 milligrams of the peptide in 220 milligrams of water in a cryotube. The material was shear oriented overnight at 40° C. in a previously described pestle-cryotube assembly. The sample was exposed to approximately 8,000 Roentgen/min γ-irradiation at the Auburn University Nuclear Science Center. Exposure was of sufficient time to achieve a $20 \times 10^6$ radiation absorbed dose (20 Mrad).

Thermoelasticity Measurements

Thermoelasticity studies were carried out on a stress-strain apparatus. Clamping of the sample in the holder was done in two stages to prevent damage to the material at the clamp edge. The sample was first gripped lightly with the top clamp, raised to 60° C. while submerged in water within the temperature jacket and allowed to equilibrate for about 2 hours. The measured force consisting of the weight of the sample and grips in water were set to zero. The bottom grip was then attached to the sample and both grips tightened to hold the sample firmly. The bottom clamp was driven as in a stress-strain measurement and stopped at 40% elongation. Force data were recorded in 5° C. steps starting at 70° C. and continuing to 40° C. where the force approached zero.

RESULTS

Temperature Profiles for Coacervation

Figure 6:
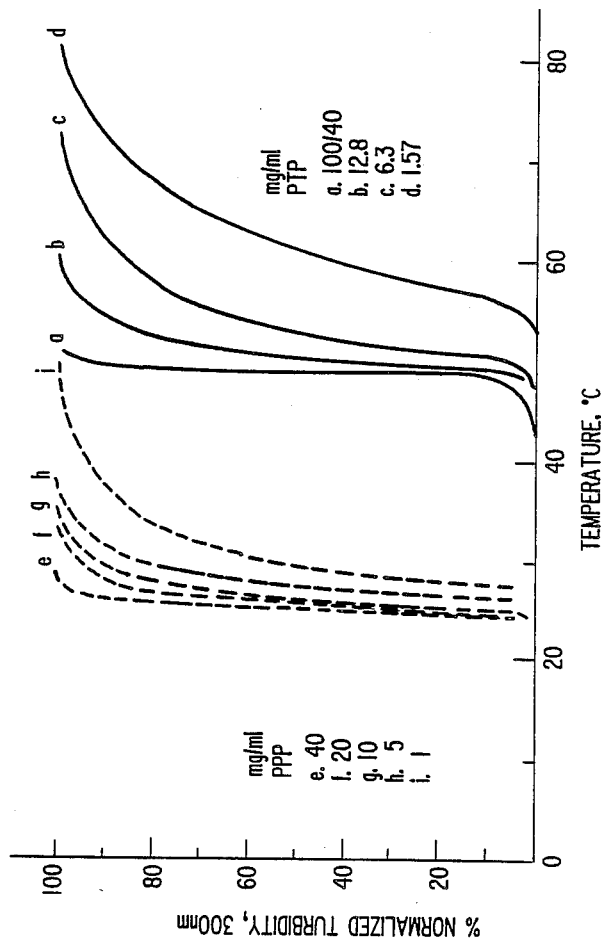

The polytetrapeptide is soluble in water in all proportions below 40° C. On raising the temperature above 40° C. the solution becomes turbid; on standing settling occurs to form a dense viscoelastic phase called a coacervate. The process is readily reversible; on lowering the temperature cloudiness clears and coacervate readily redissolves. By following the turbidity as a function of temperature, temperature profiles for coavervation are obtained which are concentration dependent. As more concentrated solutions are used, the onset of turbidity occurs at lower temperatures until further increases of concentration cause no further lowering of the temperature for onset of turbidity. The lower concentration above which raising the concentration no further lowers the temperature for onset of turbidity is called the high concentration limit. For this high moelcular weight PTP the high concentration limit is 40 mg/ml as 100 mg/ml gives the same profile. Dilution from 40 mg/ml causes a shift to higher temperature for the onset. These data are given in FIG. 6 where they are compared to similar data for the PPP. The midpoint for the high concentration limit of PTP is 49° C. whereas the value for the high concentration limit of PPP is 25° C. The decreased hydrophobicity of the tetramer results in a 24° C. increase in the temperature required to bring about the hydrophobic interactions attending aggregation.

Circular Dichroism

Figure 7:
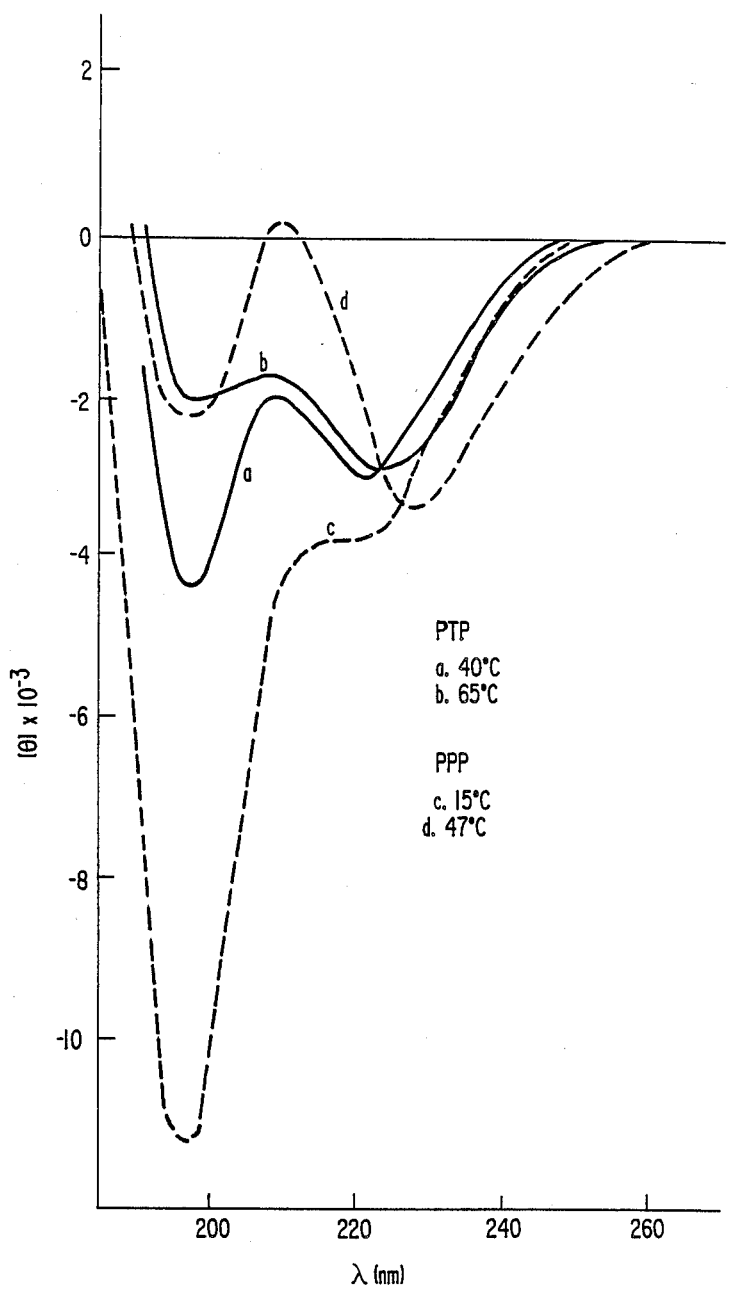

The CD spectra are shown in FIG. 7 at 40° C. (curve a) and 65° C. (curvebb) for 5 mg/ml of PTP in water. At the lower temperature there is a negative band near 220 nm and a second negative band in the 195-200 nm range. This latter band is considered to be indicative of polypeptides with limited order as fully disordered polypeptides are considered to have a negative band near 195 nm with an ellipticity of $-4 \times 10^4$. The lower magnitude of the short wavelength negative band for PTP and the negative band near 220 nm indicate some order in the PTP at 35° C. On raising the temperature the short wavelength negative band decreases in magnitude indicative of a transition toward greater intramolecular order. This transition is shown in FIG. 8A. Interestingly, its midpoint corresponds approximately to the midpoint in the temperature profile for coacervation (see FIG. 6, curve c) for a comparable concentration. It is important to note for the PTP that the change in intramolecular order precedes the intermolecular interactions, i.e., begins at a substantially lower temperature than the aggregational process followed in FIG. 6. For comparison in FIG. 7 are the CD spectra for PPP where an analogous change in spectra is observed. In this case, however, the negative band near 195 nm is much more intense making the transition toward greater order on raising the temperature more apparent. In FIG. 8A is the inverse temperature transition of PPP plotted for comparison with the PTP transition. As with the aggregational data (see FIG. 6), the temperature midpoint for the PTP intramolecular transition is shifted some 25° to higher temperatures from that of the PPP. Thus, the intramolecular ordering of the PTP is shifted to higher temperature due to the decreased hydrophobicity of the tetramer as compared to the pentamer.

Thermoelasticity Data

The temperature dependence of elastomeric force (thermoelasticity data) is plotted in FIG. 8B for 20 Mrad cross-linked PTP at an extension of 40%. There is very little elastomeric force exhibited by this matrix below 40° C. As the temperature is raised above 40° C., however, the elastomeric force develops to a maximal value near 70° C. Also included for comparison in FIG. 8B are the thermoelasticity data for a 20 Mrad cross-linked PPP matrix which exhibit a similar transition but shifted some 20° to 25° C. to lower temperatures. The development of elastomeric force, just as the temperature dependence of coacervation (see FIG. 6) and of ellipticity for the PTP, is shifted by abot 25° C. from that of the PPP. These properties are a function of the hydrophobicity of the repeating unit. Of particular interest is the comparison of the ellipticity data for the PTP with the thermoelasticity for the PTP of FIG. 8. The transition as followed by ellipticity, which is a measure of intramolecular order, begins in the range 35° to 40° C., and similarly the elastomeric force begins to develop just below 40° C. By both physical measurements the transition is essentially complete by 70° C. There is a close parallel between increase in intramolecular order and increase in elastomeric force. As the aggregational intermolecular processes, followed by turbidity, do not become significantly until nearly 50° C., it appears that the PTP matrix allows a delineation between intramolecular and intermolecular processes as related to origins of elastomeric force.

The structural features of PTP appear to be very similar to those of PPP. For example, it is clear that the same principles are operative as for the PPP. The Type II $Pro^2$-$Gly^3$ $\beta$-turn is dominant secondary structural feature and the ordering process is that of an inverse temperature transition with the optimization of intramolecular hydrophobic interactions as the temperature is raised. The perspective is again an open helix with $\beta$-turn spacers between turns of the spiral and with the Val and Pro side chains providing the intramolecular hydrophobic contacts. The suspended segment will necessarily be shorter and the librational motion will be focused on the $Gly^4$-$Val^1$ peptide moiety. Based on the cyclic conformational correlate there will be approximately 4 tetramers per turn of PTP $\beta$-spiral as opposed to the approximately 3 pentamers per turn for the PPP $\beta$-spiral.

Effect of Repeat Unit Hydrophobicity

Figure 9:
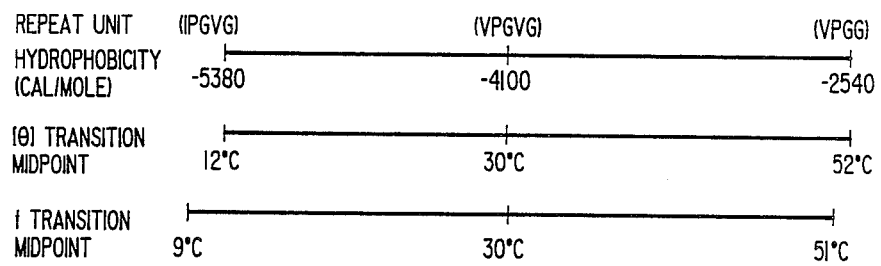

That the transitions toward increased elastomeric force are actually inverse temperature transitions dependent on the hydrophobicity of the constituent peptide is apparent from the direction of the shift of the transition on changing the hydrophobicity of the repeating unit. As the repeating unit becomes more hydrophobic, the temperature for the transition shifts to lower values. Using the Nozaki-Tanford-Bull-Breese hydrophobicity scale, the pentamer (VPGVG) would have a free energy for transfer of $-4100$ cal/mole whereas that for the tetramer (VPGG) would be $-2540$ cal/mole. For the transition $\Delta H = T\Delta S$, and for a given $\Delta H$ a higher temperature would be required if the hydrophobicity giving rise to $\Delta S$ were less. The data of FIGS. 7 and 8 show that the decreased hydrophobicity of the tetramer requires a higher temperature for the transition than for the more hydrophobic pentamer. This finding is in accordance with the above-mentioned results obtained with $Ile^1$-PPP. When $(IPGVG)_n$, or $Ile^1$-PPP, is prepared, the $Ile^1$-PPP coacervates; it increases intramolecular order on increasing the temperature and the $Ile^1$-PPP matrix increases elastomeric force on raising the temperature but the transition is shifted to 9° C. The hydrophobicity for this pentamer, (IPGVG), is $-5380$ cal/mole. In the scale plotted as FIG. 9 is the comparison of the temperature of the transition for the three polypeptide elastomers and the hydrophobicities of the repeating unit. Not only is the direction of the shift correct but the magnitude of the shift is also approximately correct. It is clear that the inverse temperature transition giving rise to the intramolecular ordering and elastomeric force development is indeed proportional to the hydrophobicity of the repeating unit, and from the detailed comparison of the transitions in FIGS. 7 and 8, it is the intramolecular process utilizing hydrophobic interactions that is responsible for the development of elastomeric force.

Thus, the bioelastomers of the present invention can encompass a wide variety of functional repeating units in order to provide a wide variation in temperature of elastomeric force development.

For example, the present bioelastomers include those having any of the following repeating units as defined above:

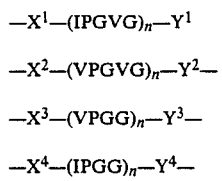

alone or in combination with each other in order to impart to the bioelastomer a capability of developing near maximum elastomeric force at a predetermined temperature.

However, also included with in the ambit of the present invention are all analogs of PPP and PTP and combinations thereof which modulate the hydrophobicity of the PPP and PTP repeating unit or units, without unduly interfering with either the formation of the viscoelastic phase or the librational motion of the polypeptide, i.e., the elasticity.

Other examples of such analogs and combinations thereof are such sequences as:

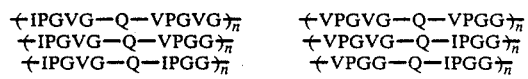

where Q is either a direct covalent bond or an interspersing amino acid residue or residues, which can be any such residue which does not interfere with the elasticity of the polypeptide.

Of course, the repeating pentapeptide sequence, as well as the repeating tetrapeptide sequence can be widely substituted to modify the repeating unit hydrophobicity, as long as the elasticity of the bioelastomer is retained. For example, the incorporated pentapeptide repeating unit can be of the general formula:

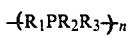

wherein $R_1$ is a peptide-producing residue selected from the group of Phe, Leu, Ile and Val; $R_2$ is such a residue selected from the group of Ala and gly; and $R_3$ is selected from the group consisting of Phe, Leu, Ile and Val; and n is an integer of from 1 to about 200; and wherein P is a L-proline-producing residue and G is a glycine-producing residue. Thus, "homopolymers" of the above pentameric sequence can be utilized or "copolymers" of the above sequence can be used in conjunction with other repeating units in keeping with this invention.

Also, in general, tetrapeptide repeating units of the formula:

$$-(R_1PGG)_n-$$

can be utilized, wherein $R_1$ and n are as defined above for the pentameric sequences. These units are incorporated into the present bioelastomers in an amount sufficient to adjust the development of elastomeric force of the bioelastomer to a predetermined temperature.

Generally, in accordance with any of the bioelastomers of the present invention, the bioelastomers can be a "homopolymer" of a functional repeating unit, such as $Phe^1$-PPP, $Ala^3$-PPP $Ile^1$-PPP, or $Ile^1$-PTP; or they can be a "copolymer" of the general formula $-(S_a-T_b)_n-$ wherein either S or T constitutes a functional repeating unit designed to modify or shift the temperature of elastomeric force development of the bioelastomer, while either S or T, whichever is remaining, constitutes another repeating unit of the bioelastomer. As noted, such "copolymers" can be of either the block or random variety, which means that a and b can each be 1 or a larger integer.

Further, for these "copolymers", it is possible, as noted, that more than one functional repeating unit can be used to modify the temperature of elastomeric force development. Thus, both units —S— and —T— in the formula above would be such repeating units, for example, $-(IPGVG)-$ and $-(VPGVG)-$. Of course, each of S and T may be comprised of a subset of repeating units of $S_i$, $S_{ii}$ and $S_{iii}$. For example, three S subsets might be PPP analogs, such as (IPGVG), (FPGVG), where F is the one letter abbreviation for Phe, or (VPAVG).

Each one of the S or T repeating units is preferably incorporate within the molar range of 1-99%. More preferably still, is the incorporation of these units within the molar range of 5-95%. However, the actual molar content of any number of different repeating units is directly proportional to the desired transition temperatures using the hydrophobicity scales as in FIG. 9.

The present bioelastomers can be used advantageously in a number of different ways which will now be described.

First, the present bioelastomers can be used in the preparation of synthetic vascular tissue or vascular prostheses. In general, such synthetic materials may be constructed in accordance with the procedures of U.S. Pat. Nos. 4,485,227 and 4,550,447, both of which are incorporated herein in their entirety.

Additionally, it appears that the bioelastomers of the present invention can be utilized in the preparation of high-frequency piezoelectric devices, utilizing the combination of a dielectric relaxation cell, a frequency source, and a force measuring device.

Essentially, a dielectric relaxation cell may be constructed in accordance with conventional techniques, except that when using the present bioelastomers, a continuous rectangular slot passes through the cell. The γ-irradiation cross-linked elastomer passes through the slot and is attached at each end for force measurement.

Additionally, it has been found that the bioelastomers of the present invention can be utilized in the preparation of high-frequency piezoelectric devices. In particular, at frequencies of about 10 MHz, the present bioelastomer peptides can follow an alternating electric field, whereby saturation and synchronization of the librational motion of the elastomers, which is considered responsible for the elastomeric force thereof, would have a profound effect on the magnitude of the elastomeric force. This, in essence, is a high-frequency piezoelectric effect. Further, the bioelastomers of the present invention have the requisite properties of elasticity and high dielectric permittivity and, on stretching, would have an axial orientation, even without flow orientation prior to cross-linking, as is also required for the piezoelectric effect.

Accordingly, the bioelastomers of the present invention may be used in the preparation of a piezoelectric device in accordance with the procedures of U.S. Pat. No. 4,565,943, which is incorporated herein in its entirety.

Interestingly, it has also been found that the present bioelastomers exhibit radar-absorbing properties. In accordance therewith, the bioelastomers of the present invention may be used in the preparation of surfaces which are radar-absorbing in accordance with U.S. Pat. No. 4,034,375, which is incorporated herein in the entirety.

Finally, as noted above, the present bioelastomers can be used in the preparation of synthetic vascular tissue. Moreover, the bioelastomers of the present invention now afford synthetic vascular materials having exceptional properties.

In particular, it has been demonstrated that certain elastin repeating sequences are chemotactic for fibroblast cells which have the capability of synthesizing elastin. For example, fibroblasts from ligamentum nuchae exhibit chemotaxis toward the elastin repeat hexapeptide sequence $-(VGVAPG)-$ with a maximal response noted at a hexapeptide concentration of about $10^{-9}$M in solution. Similarly, the nonapeptide repeating sequence of $-(AGVPGFGVG)-$ and its permutation $-(GFGVGAGVP)-$ are also chemoattractants for ligamentum nuchae fibroblasts, with maximal responses for each sequence occurring at a nonapeptide concentration of about $10^{-9}$M in solution.

Thus, in view of the above, it is specifically contemplated that the present bioelastomers can also contain amounts of the above hexapeptide and nonapeptide repeating sequences sufficient to render the synthetic vascular tissue chemotactic for fibroblast cells. These hexapeptide and nonapeptide repeating sequences can be incorporated into the present bioelastomers in accordance with standard peptide-synthesizing reactions which are well-known to peptide chemists, and as well-exemplified for the PPP and PTP analogs hereinabove. Of course, as noted above, these sequences can either be added as intact hexapeptide or nonapeptide sequences to the bioelastomers, or they can be generated by the step-wise addition of a single amino acid residue at a time by solid-phase automated synthesis.

The precise amount of chemotactic sequences incorporated into the bioelastomer depends, of course, on the desired response intensity. However, in general, in order for the synthetic vascular tissue to exhibit sufficient fibroblastic chemotaxis, it is desirable that the total peptide sequence of the bioelastomer comprise at least $10^{-11}$ molar % of the chemotactic sequences. Conversely, it will usually not be necessary to exceed about 1 molar % of the chemotactic sequences based on the total peptide content. However, as noted this amount can easily be adjusted by experimentation to obtain the optimal amount required.

Additionally, it is noted that the term "and units thereof modified by hexapeptide units" refers to the fact that the tetrapeptide and pentapeptide repeating units of the present bioelastomers can be modified by the addition of hexapeptide repeating units thereto for the purpose of enhancing the mechanical strength of the bioelastomer. Of course, an example of such an added hexameric unit is the sequence $-\!\!(\text{APGVGV})\!\!-_n$, where A, P, V and G are as defined throughout this disclosure, and n is an integer of about 1 to 50, and which varies depending upon the properties desired.

Finally, it is noted that for all of the bioelastomers of the present invention having incorporated therein one or more functional repeating units of the formula:

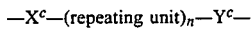

where c is an integer of from 1-4 as used throughout this disclosure, and is the same value for X and Y when used, that n is an integer of from 1 to about 200, but can also have a value of 0, when $X^c$ and $Y^c$ together constitute, theselves, at least one repeating unit.

The present bioelastomers contain elastomeric units, in addition to the units which are incorporated to modify the transition temperature, which can be a copolymer of pentapeptide "monomer" units and modifying hexapeptide "monomer" units; tetrapeptide "monomer" units and modifying hexapeptide "monomer" units; or pentapeptide, tetrapeptide, and "monomer" units thereof modified by hexapeptide monomer units.

Additionally, as noted above, the elastomeric units of these bioelastomers may also contain other hexapeptide and nonapeptide sequences which exhibit fibroblastic chemotaxis, in order to render the entire bioelastomer and synthetic vascular tissue or protheses made therefrom chemotactic for fibroblasts.

Finally, although the value of n is the above formulas is generally 1 to 200, it is possible that n can be 0, with the proviso that the units $X^c$ and $Y^c$ attached to the functional repeating unit, themselves constitute at least one such repeating unit, in an amount sufficient to adjust the elastomeric force development of the bioelastomer to a predetermined temperature.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A bioelastomer containing repeating units selected from the group consisting of elastomeric tetrapeptide, or pentapeptide or units thereof modified by hexapeptide repeating units and mixtures thereof, wherein said repeating units comprise amino acid residues selected from the group consisting of hydrophobic amino acid and glycine residues, wherein said repeating units exist in a conformation having a β-turn which comprises a polypentapeptide unit of the formula:

wherein
I is a peptide-forming residue of L-isoleucine;
P is a peptide-forming residue of L-proline;
G is a peptide-forming residue of glycine;
V is a peptide-forming residue of L-valine; and
wherein $X^1$ is PGVG, GVG, VG, G or a covalent bond; $Y^1$ is IPGV, IPG, IP, I or a covalent bond; and n is an integer from 1 to 200, or n is 0, with the proviso that $X^1$ and $Y^1$ together constitute at least one of said pentameric unit in an amount sufficient to adjust the development of elastomeric force of the bioelastomer to a predetermined temperature.

2. A method of decreasing the temperature of elastomeric force development of a bioelastomer containing repeating units selected from the group consisting of elastomeric tetrapeptide, or pentapeptide or units thereof modified by hexapeptide repeating units and mixtures thereof, wherein said repeating units comprise amino acid residues selected from the group consisting of hydrophobic amino acid and glycine residues, wherein said repeating units exist in a conformation having a β-turn which comprises a polypentapeptide unit of the formula:

wherein
I is a peptide-forming residue of L-isoleucine;
P is a peptide-forming residue of L-proline;
G is a peptide-forming residue of glycine;
V is a peptide-forming residue of L-valine; and
wherein $X^1$ is PGVG, GVG, VG, G or a covalent bond; $Y^1$ is IPGV, IPG, IP, I or a covalent bond; and n is an integer from 1 to 200, or n is 0, with the proviso that $X^1$ and $Y^1$ together constitute at least one of said pentameric unit in an amount sufficient to adjust the development of elastomeric force of the bioelastomer to a predetermined temperature.

3. A bioelastomer containing repeating units selected from the group consisting of elastomeric tetrapeptide, or pentapeptide or units thereof modified by hexapeptide repeating units and mixtures thereof, wherein said repeating units comprise amino acid residues selected from the group consisting of hydrophobic amino acid and glycine residues, wherein said repeating units exist in a conformation having a β-turn which comprises:

(A) a polypentapeptide unit of the formula:

and
(B) a polypentapeptide unit of the formula:

wherein
I is a peptide-forming residue of L-isoleucine;
P is a peptide-forming residue of L-proline;
G is a peptide-forming residue of glycine;
V is a peptide-forming residue of L-valine; and
wherein $X^1$ and $X^2$ are each PGVG, GVG, VG, G or a covalent bond; $Y^1$ is IPGV, IPG, IP, I or a covalent bond; and n is an integer from 1 to 200, or n is 0, with the proviso that $X^1$ and $Y^1$ or $X^2$ and $Y^2$ together constitute at least one of said pentameric unit in an amount sufficient to adjust the development of elastomeric force of the bioelastomer to a predetermined temperature.

4. A method of adjusting the temperature of elastomeric force development of a bioelastomer containing repeating units selected from the group consisting of elastomeric tetrapeptide, or pentapeptide or units thereof modified by hexapeptide repeating units and mixtures thereof, wherein said repeating units comprise amino acid residues selected from the group consisting of hydrophobic amino acid and glycine residues, wherein said repeating units exist in a conformation having a β-turn which comprises a polypentapeptide unit of the formula:

$$-X^1-(IPGVG)_n-Y^1-$$

or a polypentapeptide unit of the formula:

$$-X^2-(VPGVG)_n-Y^2-$$

or a mixture thereof, wherein for the above formulas,
I is a peptide-forming residue of L-isoleucine;
P is a peptide-forming residue of L-proline;
G is a peptide-forming residue of glycine;
V is a peptide-forming residue of L-valine; and
wherein $X^1$ and $X^2$ are each PGVG, GVG, VG, G or a covalent bond; $Y^1$ is IPGV, IPG, IP, I or a covalent bond; and n is an integer from 1 to 200, or n is 0, with the proviso that $X^1$ and $Y^1$ or $X^2$ and $Y^2$ together constitute at least one of said pentameric unit in an amount sufficient to adjust the development of elastomeric force of the bioelastomer to a predetermined temperature.

5. A bioelastomer containing repeating units selected from the group consisting of elastomeric tetrapeptide, or pentapeptide or units thereof modified by hexapeptide repeating units and mixtures thereof, wherein said repeating units comprise amino acid residues selected from the group consisting of hydrophobic amino acid and glycine residues, wherein said repeating units exist in a conformation having a β-turn which comprises a tetrapeptide unit of the formula:

$$-X^3-(IPGVG)_n-Y^3-$$

wherein
$X^3$ is PGG, GG, G or a covalent bond;
$Y^3$ is VPG, VP, V OR a covalent bond; and V is a peptide-producing residue of L-valine; P is a peptide-producing residue of L-proline; and G is a peptide-producing residue of glycine; and n is an integer from 1 to 200, or n is 0, with the proviso that $X^3$ and $Y^3$ together constitute at least one of said tetrameric unit, in an amount sufficient to increase the temperature at which the elastomeric force of the bioelastomer develops.

6. A bioelastomer containing repeating units selected from the group consisting of elastomeric tetrapeptide, or pentapeptiude or units thereof modified by hexapeptide repeating units and mixutres thereof, wherein said repeating units comprise amino acid residues selected from the group consisting of hydrophobic amino acid and glycine residues, wherein said repeating units exist in a conformation having a β-turn which comprises incorporating into said bioelastomer a tetrapeptide unit of the formula:

$$-X^3-(IPGVG)_n-Y^3-$$

wherein
$X^3$ is PGG, GG, G or a covalent bond;
$Y^3$ is VPG, VP, V OR a covalent bond; and V is a peptide-producing residue of L-valine; P is a peptide-producing residue of L-proline; and G is a peptide-producing residue of glycine; and n is an integer from 1 to 200, or n is 0, with the proviso that $X^3$ and $Y^3$ together constitute at least one of said tetrameric unit, in an amount sufficient to adjust the development of elastomeric force of the bioelastomer to a predetermined temperature.

7. A bioelastomer containing repeating units selected from the group consisting of elastomeric tetrapeptide, or pentapeptide or units thereof modified by hexapeptide repeating units and mixtures thereof, wherein said repeating units comprise amino acid residues selected from the group consisting of hydrophobic amino acid and glycine residues, wherein said repeating units exist in a conformation having a β-turn which comprises a polypentapeptide unit of the formula:

$$-X^4-(IPGG)_n-Y^4-$$

wherein $X^4$ is PGG, GG G or a covalent bond; $Y^4$ is IPG, IP, I or a covalent bond; and
I is a peptide-forming residue of L-isoleucine;
P is a peptide-forming residue of L-proline;
G is a peptide-forming residue of glycine; and n is an integer from 1 to 200, or n is 0, with the proviso that $X^4$ and $Y^4$ together constitute at least one of said pentameric unit in an amount sufficient to adjust the development of elastomeric force of the bioelastomer to a predetermined temperature.

8. A method of adjusting the temperature of elastomer force development of a bioelastomer containing repeating units selected from the group consisting of elastomeric tetrapeptide, or pentapeptide or units thereof modified by hexapeptide repeating units and mixtures thereof, wherein said repeating units comprise amino acid residues selected from the group consisting of hydrophobic amino acid and glycine residues, wherein said repeating units exist in a conformation having a β-turn which comprises a polypentapeptide unit of the formula:

$$-X^4-(IPGVG)_n-Y^4-$$

wherein $X^4$ is PGG, GG, G or a covalent bond; $Y^4$ is IPG, IP, I or a covalent bond; and
I is a peptide-forming residue of L-isoleucine;
P is a peptide-forming residue of L-proline;
G is a peptide-forming residue of glycine; and n is an integer from 1 to 200, or n is 0, with the proviso that $X^4$ and $Y^4$ together constitute at least one of said pentameric unit in an amount sufficient to adjust the development of elastomeric force of the bioelastomer to a predetermined temperature.

9. A bioelastomer containing repeating units selected from the group consisting of elastomeric tetrapeptide, or pentapeptide or units thereof modified by hexapeptide repeating units and mixtures thereof, wherein said repeating units comprise amino acid residues selected from the group consisting of hydrophobic amino acid and glycine residues, wherein said repeating units exist in a conformation having a β-turn which comprises a tetra peptide or a polypentapeptide unit or mixture thereof or repeating units thereof, capable of adjusting the temperature at which elastomeric force of the bioelastomer develops, in an amount sufficient to adjust the development of elastomeric force of said bioelastomer to a predetermined temperature, with the proviso that the elasticity of the bioelastomer is retained.

10. A bioelastomer according to claim 9, which further comprises a fibroblastic chemotactic hexapeptide or a nonapeptide unit or repeating units an amount sufficient to impart fibroblastic chemotactic properties to said bioelastomer.

11. The bioelastomer according to claim 10, wherein said chemotactic hexapeptide unit is ─(VGVAPG)─, and said chemotactic nonapeptide sequences are ─(AGvPGFGVG)─ and ─(GFGVGAGVP)─.

12. A bioelastomer containing repeating units selected from the group consisting of elastomeric tetrapeptide, or pentapeptide or units thereof modified by hexapeptide repeating units and mixtures thereof, wherein said repeating units comprise amino acid residues selected from the group consisting of hydrophobic amino acid and glycine residues, wherein said repeating units exist in a conformation having a β-turn which comprises a polypentapeptide unit of the formula:

wherein $R_1$ is a peptide-producing residue selected from the group consisting of Phe, Leu, Ils, and Val; $R_2$ is such a residue selected from the group consisting of Ala and Gly; $R_3$ is such a residue selected from the group consisting of Phe, Leu, Ile, and Val; P is a L-proline-producing residue, and G is a glycine-producing residue, and n is an integer from 1 to 200, in an amount sufficient to adjust the development of elastomeric force of said bioelastomer to a predetermined temperature.

13. The bioelastomer of claim 12, which further comprises a fibroblastic chemotactic hexapeptide or nonapeptide unit or repeating units in an amount sufficient to impart fibroblastic chemotactic properties to said bioelastomers.

14. A method of adjusting the temperature of elastomeric force development of a bioelastomer containing repeating units selected from the group consisting of elastomeric tetrapeptide, or pentapeptide or units thereof modified by hexapeptide repeating units and mixtures thereof, wherein said repeating units comprise amino acid residues selected from the group consisting of hydrophobic amino acid and glycine residues, and wherein said repeating units exist in a conformation having a β-turn, which comprises incorporating into said bioelastomer a tetrapeptide or pentapeptide unit or mixtures thereof or repeating units thereof, capable of adjusting the temperature at which elastomeric force of the bioelastomer develops, in an amount sufficient to adjust the delvelopment of elastomeric force of said bioelastomer, with the proviso that the elasticity of the bioelastomer is retained.

15. A method of adjusting the temperature of elastomeric force development of a bioelastomer containing repeating units selected from the group consisting of elastomeric tetrapeptide, or pentapeptide or units thereof modified by hexapeptide repeating units and mixtures thereof, wherein said repeating units comprise amino acid residues selected from the group consisting of hydrophobic amino acid and glycine residues, wherein said repeating units exist in a conformation having a β-turn which comprises a polypentapeptide unit of the formula:

wherein $R_1$ is a peptide-producing residue selected from the group consisting of Phe, Leu, Ils, and Val; $R_2$ is such a residue selected from the group consisting of Ala and Gly; $R_3$ is such a residue selected from the group consisting of Phe, Leu, Ile, and Val; P is a L-proline-producing residue, and G is a glycine-producing residue, and n is an integer from 1 to 200, in an amount sufficient to adjust the development of elastomeric force of said bioelastomer to a predetermined temperature.

16. A bioelastomer containing repeating units selected from the group consisting of elastomeric tetrapeptide, or pentapeptide or units thereof modified by hexapeptide repeating units and mixtures thereof, wherein said repeating units comprise amino acid residues selected from the group consisting of hydrophobic amino acid and glycine residues, wherein said repeating units exist in a conformation having a β-turn which comprises a polypentapeptide unit of the formula:

─(R₁PGG)─ₙ wherein $R_1$ is a peptide-producing residue selected from the group consisting of Phe, Leu, Ils, and Val; P is a L-proline-producing residue, and G is a glycine-producing residue, and n is an integer from 1 to 200, in an amount sufficient to adjust the development of elastomeric force of said bioelastomer to a predetermined temperature.

17. A method of adjusting the temperature of elastomeric force development of a bioelastomer containing repeating units selected from the group consisting of elastomeric tetrapeptide, or pentapeptide or units thereof modified by hexapeptide repeating units and mixtures thereof, wherein said repeating units comprise amino acid residues selected from the group consisting of hydrophobic amino acid and glycine residues, wherein said repeating units exist in a conformation having a β-turn which comprises a polypentapeptide unit of the formula:

wherein $R_1$ is a peptide-producing residue selected from the group consisting of Phe, Leu, Ils, and Val; P is a L-proline-producing residue, and G is a glycine-producing residue, and n is an integer form 1 to 200, in an amount sufficient to adjust the development of elastomeric force of said bioelastomer to a predetermined temperature.

18. The bioelastomer of claim 1, which is substantially cross-linked.

19. The bioelastomer of claim 3, which is substantially cross-linked.

20. The bioelastomer of claim 5, which is substantially cross-linked.

21. The bioelastomer of claim 7, which is substantially cross-linked.

22. The bioelastomer of claim 9, which is substantially cross-linked.

23. The bioelastomer of claim 12, which is substantially cross-linked.

24. The bioelastomer of claim 16, which is substantially cross-linked.

* * * * *

UNITED STATES PATENT AND TRADEMARK OFFICE
CERTIFICATE OF CORRECTION

PATENT NO. : 4,783,523
DATED : November 8, 1988
INVENTOR(S) : Dan W. Urry

It is certified that error appears in the above-indentified patent and that said Letters Patent is hereby corrected as shown below:

In Column 33, Claim 5, line 11, change that portion of the chemical formula reading "(IPGVG)" to read "(VPGG)". In Column 33, Claim 6, line 1, before the phrase "bioelastomer containing repeating" insert the phrase "method of adjusting the temperature of elastomeric force development of a". In Column 33, Claim 6, line 12, change that portion of the chemical formula reading "(IPGVG)" to read "(VPGG)".

In Column 34, Claim 7, line 9, replace the word "polypentapeptide" with the word "tetrapeptide". In Column 34, Claim 8, line 10, replace the phrase "a polypentapeptide" with "incorporating into said bioelastomer a tetrapeptide". In Column 34, Claim 8, line 13, change that portion of the chemical formula "(IPGVG)" to read "(IPGG)".

In Column 36, Claim 15, line 1, replace the phrase "a polypentapeptide" with "incorporating into said bioelastomer a pentapeptide". In Column 36, Claim 15, line 7, replace the abbreviation "IIs" with the amino acid abbreviation "Ile". In Column 36, Claim 16, line 9, replace the word "polypentapeptide" with the phrase "tetrapeptide repeating". In Column 36, Claim 17, line 10, replace the phrase "a polypentapeptide" with the phrase "incorporating into said bioelastomer a tetrapeptide". In Column 36, Claim 17, line 16, replace the abbreviation "IIs" with the amino acid abbreviation "Ile".

Signed and Sealed this

Twentieth Day of December, 1994

Attest:

BRUCE LEHMAN

Attesting Officer   Commissioner of Patents and Trademarks